(12) United States Patent
Dai et al.

(10) Patent No.: US 7,662,976 B2
(45) Date of Patent: Feb. 16, 2010

(54) TRIPTOLIDE DERIVATIVES FOR MODULATION OF APOPTOSIS AND IMMUNOSUPPRESSION

(75) Inventors: Dongcheng Dai, Mountain View, CA (US); John H. Musser, San Carlos, CA (US); Edwin S. Lennox, Stanford, CA (US)

(73) Assignee: Pharmagenesis, Inc., Redwood City, CA (US)

(*) Notice: Subject to any disclaimer, the term of this patent is extended or adjusted under 35 U.S.C. 154(b) by 0 days.

(21) Appl. No.: 12/366,528

(22) Filed: Feb. 5, 2009

(65) Prior Publication Data

US 2009/0171103 A1 Jul. 2, 2009

Related U.S. Application Data

(62) Division of application No. 10/478,777, filed as application No. PCT/US03/17177 on May 29, 2003.

(60) Provisional application No. 60/384,480, filed on May 31, 2002.

(51) Int. Cl.
*C07D 307/77* (2006.01)
(52) U.S. Cl. ....................................... 549/297
(58) Field of Classification Search ................ 549/297
See application file for complete search history.

(56) References Cited

U.S. PATENT DOCUMENTS

| | | | |
|---|---|---|---|
| 3,646,201 A | 2/1972 | Kallianos et al. | |
| 4,005,108 A | 1/1977 | Kupchan | |
| 5,192,817 A | 3/1993 | Takaishi et al. | |
| 5,294,443 A | 3/1994 | Lipsky et al. | |
| 5,430,054 A | 7/1995 | Qian et al. | |
| 5,468,772 A | 11/1995 | Xu et al. | |
| 5,565,569 A | 10/1996 | Tsujihara et al. | |
| 5,580,562 A | 12/1996 | Lipsky et al. | |
| 5,648,376 A | 7/1997 | Strobel et al. | |
| 5,663,335 A | 9/1997 | Qi et al. | |
| 5,759,550 A | 6/1998 | Weidmann et al. | |
| 5,843,452 A | 12/1998 | Weidmann et al. | |
| 5,919,816 A | 7/1999 | Hausheer et al. | |
| 5,962,516 A | 10/1999 | Qi et al. | |
| 5,972,998 A | 10/1999 | Jung et al. | |
| 6,004,999 A | 12/1999 | Jung et al. | |
| 6,150,539 A | 11/2000 | Musser | |
| 6,294,546 B1 | 9/2001 | Rosen et al. | |
| 6,329,148 B1 | 12/2001 | Rosen et al. | |
| 6,458,537 B1 | 10/2002 | Staub et al. | |
| 6,537,984 B2 | 3/2003 | Rosen et al. | |
| 6,548,537 B1 | 4/2003 | Dai et al. | |
| 6,569,893 B2 * | 5/2003 | Dai et al. ................ | 514/468 |
| 6,599,499 B1 | 7/2003 | Rosen et al. | |
| 6,620,843 B2 | 9/2003 | Fidler et al. | |
| 6,777,441 B2 | 8/2004 | Wang et al. | |
| 6,943,259 B2 | 9/2005 | Dai et al. | |
| 7,019,151 B2 | 3/2006 | Dai et al. | |
| 7,098,348 B2 | 8/2006 | Dai et al. | |
| 7,417,069 B2 | 8/2008 | Dai et al. | |
| 2002/0077350 A1 | 6/2002 | Babish et al. | |
| 2004/0018260 A1 | 1/2004 | Ren et al. | |
| 2004/0152767 A1 | 8/2004 | Dai et al. | |
| 2004/0198808 A1 | 10/2004 | Dai et al. | |
| 2004/0235943 A1 | 11/2004 | Dai et al. | |
| 2005/0288645 A1 | 12/2005 | LaVon | |
| 2007/0244080 A1 | 10/2007 | Fidler et al. | |
| 2007/0249048 A1 | 10/2007 | Dai et al. | |
| 2007/0282114 A1 | 12/2007 | An et al. | |
| 2008/0193948 A1 | 8/2008 | Fidler et al. | |
| 2008/0287530 A1 | 11/2008 | Yuan et al. | |

FOREIGN PATENT DOCUMENTS

| | | |
|---|---|---|
| CN | 1052859 A | 7/1991 |
| CN | 1317248 A | 10/2001 |
| EP | 0 156 643 B1 | 10/1985 |
| JP | 61-085319 | 4/1986 |
| JP | 03 178977 | 8/1991 |
| WO | WO 94/26265 A1 | 11/1994 |
| WO | WO 97/31920 A1 | 9/1997 |
| WO | WO 97/31921 A1 | 9/1997 |
| WO | WO 98/52933 A1 | 11/1998 |
| WO | WO 98/52951 A1 | 11/1998 |
| WO | WO 00/12483 A1 | 3/2000 |
| WO | WO 00/63212 | 10/2000 |
| WO | WO 01/15707 A1 | 3/2001 |

(Continued)

OTHER PUBLICATIONS

Aumuller, G. et al., "Intermediate filaments in sertoli cells", *Microscopy Research and Technique*, 20:50-72(1992).
Becker, K. et al., "Thioredoxin reductase as a pathophysiological factor and drug target", *Eur. J. Biochem.*, 267(20):6118-6125 (2000).
Berg, D. et al., "14-3-3 Proteins in the nervous system", *Nature Reviews Neuroscience*, 4:752-62 (2003).
Britton, R. et al., "New okadaic acid analogues from the marine sponge Merriamum oxeato and their effect on mitosis", *J. Nat. Prod.*, 66:838-43 (2003).
Chang, W-T. et al., "Triptolide and chemotherapy cooperate in tumor cell apoptosis. A role for the p53 pathway", *The Journal of Biological Chemistry*, 276(3):2221-2227 (2001).

(Continued)

*Primary Examiner*—D. Margaret Seaman
*Assistant Examiner*—Nizal S Chandrakumar
(74) *Attorney, Agent, or Firm*—King & Spalding LLP; Peter J. Dehlinger; Susan J. Myers Fitch

(57) ABSTRACT

Variously substituted carbonate and carbamate derivatives of triptolide compounds have good aqueous solubility and convert to biologically active compounds in vivo, at a rate which can be modulated by varying the substitution on the prodrug. The prodrugs are useful as immunosuppressive, anti-inflammatory and anticancer agents.

12 Claims, 5 Drawing Sheets

FOREIGN PATENT DOCUMENTS

| WO | WO 02/56835 A2 | 7/2002 |
|---|---|---|
| WO | WO 02/070472 A1 | 9/2002 |
| WO | WO 02/074759 A1 | 9/2002 |
| WO | WO 03/101951 A2 | 12/2003 |
| WO | WO 2005/000291 A1 | 1/2005 |
| WO | WO 2005/020887 A2 | 3/2005 |
| WO | WO 2005/062913 A2 | 7/2005 |
| WO | WO 2005/084365 A2 | 9/2005 |
| WO | WO 2006/012204 A2 | 2/2006 |
| WO | WO 09/23201 A1 | 2/2009 |

OTHER PUBLICATIONS

Chen et al., "Mechanisms of tolerance induced by PG490-88 in a bone marrow transplantation model", *Transplantation*, 73(1):115 (2002).

Chen et al., "Prevention of graft-versus-host disease by a novel immunosuppressant, PG490-88, through inhibition of alloreactive T cell expansion", *Transplantation*, 70(10):1442-1447 (2000).

Cheng et al., "Research on extraction technology of Tripterygium", *Chinese Journal of Pharmaceuticals*, 21(10):435-436 (No English translation) (1990).

Cheng, X.X. et al., Yao Xue Xue Bao, *ACTA Pharmaceutica Sinica*, 37:339-342 (2002) (English Abstract translation).

Englebienne et al., *Drug Design Reviews -Online*, "The Place of Biosteric Sila Substitution in Drug Design", 2 pages (2005).

Fidler, J.M. et al., "PG490-88, a derivative of triptolide, causes tumor regression and sensitizes tumors to chemotherapy", *Molecular Cancer Therapeutics*, 2(9):855-62 (2003).

Fidler, J.M. et al., "Immunosuppressive activity of the Chinese medicinal plant Tripterygium wilfordii. III. Suppression of graft-versus-host disease in murine allogeneic bone marrow transplantation by the PG27 extract", *Transplantation*, 74(4):445-457 (2002).

Fruman, D.A. et al., "Phosphoinositide Kinases", *Ann. Rev. Biochem.*, 67:481-507 (1998).

Fu et al., "14-3-3 Proteins: Structure, Function, and regulation", *Ann. Rev. Pharmacol. Toxicol.*, 40:617-47 (2000).

Gabbiani, G., "The myofibroblast in wound healing and fibrocontractive diseases", *Journal of Pathology*, 200:500-503 (2003).

Garcia, A. et al., "Serine/threonine protein phosphatases PP1 and PP2A are key players in apoptosis", *Biochimie*, 85:721-726 (2003).

Gilles, C. et al., "Transactivation of vimentin by beta-catenin in human breast cancer cells", *Cancer Research*, 63(10):2658-2664 (2003).

Gleichmann, E. et al., "Graft-versus-host reactions: clues to the etiopathology of a spectrum of immunological diseases", *Immunology Today*, 5(11):324-332 (1984).

Goto, Y. et al., "Augmented cytoplasmic Smad4 induces acceleration of TGF-beta1 signaling in renal tubulointerstitial cells of hereditary nephrotic ICGN mice with chronic renal fibrosis; possible role for myofibroblastic differentiation", *Cell Tissue Res.*, 315:209-221 (2004).

Gross, T.J. and Hunninghake, G.W., "Idiopathic pulmonary fibrosis", *N. Engl. J. Med.*, 345(7):517-525 (2001).

He, Q. et al., "Neuroprotective eggects of Tripterygium wilfordii Hook F Monomer $T_{10}$ on glutamate induced PC12 cell line damage and its mechanism", *Beijing Da Xue Xue Bao, Journal of Peking University (Health Sciences)*, 35(3):252-5 (Jun. 2003) (English Abstract Translation).

Houtman, J.C. et al., "Early phosphorylation kinetics of proteins involved in proximal TCR-mediated signaling pathways", *Journal of Immunology*, 175(4):2449-2458 (2005).

Jiang, X-H. et al., "Functional p53 is required for triptolide-induced apoptosis and AP-1 and nuclear factor-kappaB activation in gastric cancer cells",*Oncogene*, 20(55):8009-8018 (2001).

Jerums, G. at al., "Evolving concepts in advanced glycation, diabetic nephropathy, and diabetic vascular disease", *Archives of Biochemistry and Biophysics*, 419(1):55-62 (2003).

Jiarun, Z. et al., "Screening of active anti-inflammatory, immunosuppressive and antifertility components of Tripterygium wilfordii", *ACTA Academiae Medicinae Sinicae* 13(6):391-397 (English Abstract only) (1991).

Jones, S.L. et al. "A role for the actin-bundling protein L-plastin in the regulation of leukocyte integrin function", *Proc. Natl. Acad. Sci. USA*, 95(16):9331-9336 (1998).

Kershenobich, D. et al., "Concise Review: Liver fibrosis and inflammation. A review", *Annals of. Hepatology*, 2(4):159-163 (2003).

Keyser, F. D. et al., "The role of T cells in Rheumatoid Arthritis", *Clinical Rgeumatology*, 14(Suppl 2):5-9 (1995).

Khanna, A.K. and Mehta, M.R., "Targeted in vitro and in vivo gene transfer into T lymphocytes: potential of direct inhibition of alloimmune activation", *BMC Immunology*, 7(26):1-10 (2006).

Korngold, B. and Sprent, J. "Lethal graft-versus-host disease after bone marrow transplantation across minor histocompatibility barriers in mice. Prevention by removing mature T cells from marrow", *J. Exp. Med.*, 148:1687-98 (1978).

Kupchan S.M. et al., "Triptolide and tripdiolide, novel antileukemic diterpenoid triepoxides from Tripterygium wilfordii", *American Chemical Society*, 94(20):7194-7195 (1972).

Kurz, E.U. et al., "Modulation of human DNA topoisomerase IIalpha function by interaction with 14-3-3epsilon", *The Journal of Biological Chemistry*, 275(18):13948-13954 (2000).

Kutney, J.P. et al., "Studies with plant cell cultures of the Chinese herbal plant, Tripterygium wilfordii, Synthesis and biotransformation of diterpene analogues", *Heterocycles*, 44(1):2-11 (1997).

Larribere, L. et al., "PI3K mediates protection against Trail-induced apoptosis in primary human melanocytes", *Cell Death and Differentiation*, 11(10):1084-1091 (2004).

Leonard, C.T. et al., "PG490-88, a derivative of triptolide, attenuates obliterative airway disease in a mouse heterotopic tracheal allograft model", *Journal of Heart and Lung Transplantation*, 21(12):1314-1318 (2002).

Leuenroth, S.J. and Crews, C.M., "Studies on calcium dependence reveal multiple modes of action for triptolide", *Chemistry and Biology*, 12(12):1259-1268 (2005).

Li, K.K. and Fidler, J.M., "PG490-88 erxerts 1-16 potent anticancer activity alone and in combination therapy in a nude mouse xenograft model", Proceedings of the American Association for Cancer Research Annual Meeting Mar. 2001, 42:73, Abstract #391 (2001).

Li, F-Q. et al., "Neurotrophic and neuroprotective effects of tripchlorolide, an extract of Chinese herb Tripterygium wilfordii Hook F, on dopaminergic neurons", *Experimental Neurology*, 179(1):28-37 (2003).

Li, F-Q. et al., "Triptolide, a Chinese herbal extract, protects dopaminergic neurons from inflammation-mediated damage through inhibition of microglial activation", *Journal of Neuroimmunology*, 148(1-2):24-31 (2004).

Lin, C.S. et al., "Upregulation of L-plastin gene by testosterone in breast and prostate cancer cells: identification of three cooperative androgen receptor-binding sequences", *DNA Cell Biology*, 19(1):1-7 (2000).

List, A.F. et al., "Vascular endothelial growth factor receptor-1 and receptor-2 initiate a phosphatidylinositide 3-kinase-dependent clonogenic response in acute myeloid leukemia cells.", *Experimental Hematology*, 32(6):526-535 (2004).

Lowell, M.A. et al. "Decreased thioredoxin and increased thioredoxin reductase levels in Alzheimer's disease brain", *Free Radical Biology & Medicine*, 28(3):418-27 (2000).

Lundstrom, J. et al., "A Pro to His in active site of thioredoxin increases its disulfide-isomerase activity 10-fold. New refolding systems for reduced or randomly oxidized ribonuclease", *The Journal of Biological Chemistry*, 267(13):9047-9052 (1992).

Lundy, S.K. et al., "Cells of the synovium in rheumatoid arthritis", *Arthritis Research & Therapy*, 9(1):1-11 (2007).

Mason et al., "Pharmacological therapy fir idiopathic pulmonary fibrosis", *Am. J. Respir. Crit. Care Med.*, 160:1771-1777 (1999).

Masters, S.C. and Fu, H., "14-3-3 Proteins mediate an essential anti-apoptotic signal", *The Journal of Biological Chemistry*, 276(48):45193-45200 (2001).

Matlin, S.A. et al., "Male antifertility compounds from Tripterygium wilfordi Hook F.", *Contraception*, 47:387-400 (1993).

Mesa, R.A. et al., "In vitro antiproliferative activity of the farnesyltransferase inhibitor R115777 in hematopoietic progenitors from patients with myelofibrosis with myeloid metaplasia", *Leukemia*, 17(5):849-55 (2003).

Gu, Ming et al., "Effect of Chinese herb *Tripterygium wilfordii* Hook F monomer triptolide on apoptosis of PC12 cells induced by Aβ1-42" *ACTA Physiologica Sinica*, 56(1):73-78 (2004) (English Abstract translation).

Murase, N. et al., "Hamster-to-rat heart and liver xenotransplantation with FK506 plus antiproliferative drugs", *Transplantation*, 55(4):701-708 (1993).

Ning, L. et al., "Biotransformation of triptolide by Cunninghamella blakesleana", Tetrahedron, 59(23):4209-4213 (2003).

Ono, K. and Lindsey, E.S., "Improved technique of heart transplantation in rats", *Journal of Thoracic and Cardiovascular Surgery*, 57(2):225-29 (1969).

Ory, S. et al., "Protein phosphatase 2A positively regulates Ras signaling by dephosphorylating KSR1 and Raf-1 on critical 14-3-3 binding sites", *Current Biology*, 13(16):1356-1364 (2003).

Otsuka, M. et al., "Differential expression of the L-plastin gene in human colorectal cancer progression and metastasis", *Biochemical and Biophysical Research Communications*, 289(4):876-881 (2001).

Pei, J-J. et al. "Okadaic-acid-induced inhibition of protein phosphatase 2A produces activation of mitogen-activated protein kinases ERK1/2, MEK1/2, and p70 S6, similar to that in Alzheimer's disease", *American Journal of Pathology*, 163(3):845-858 (2003).

Powis, G. and Montfort, W.R., "Properties and biological activities of thioredoxins", *Ann.Rev. Pharmacol. Toxicol.*, 41:261-295 (2000).

Qiu, D. and Kao, P.N., "Immunosuppressive and anti-inflammatory mechanisms of triptolide, the principal active diterpenoid from the Chinese medicinal herb *Tripterygium wilfordii* Hook. f.", *Drugs R&D*, 4(1):1-18 (2003).

Qiu, D. et al., "Immunosuppressant PG490 (triptolide) inhibits T-cell interleukin-2 expression at the level of purine-box/nuclear factor of activated T-cells and NF-kappaB transcriptional activation", *The Journal of Biological Chemistry*, 274(19):13443-13450 (1999).

Redpath, N.T. et al., "Regulation of translation elongation factor-2 by insulin via a rapamycin-sensitive signalling pathway", *The EMBO Journal*, 15(9):2291-2297 (1996).

Reichert, T.E. et al., "Interleukin-2 expression in human carcinoma cell lines and its role in cell cycle progression", *Oncogene*, 19(4):514-525 (2000).

Sato, S. et al., "Modulation of Akt kinase activity by binding to Hsp90", *Proc Natl Acad Sci USA*, 97(20):10832-10837 (2000).

Schlesinger, C. et al., "Constrictive (obliterative) bronchiolitis: diagnosis, etiology, and a critical review of the literature", *Annals of Diagnostics Pathology*,. 2(5):321-34 (1998).

Schlesinger, C. et al., "Constrictive (obliterative) bronchiolitis", *Current Opinion in Pulmonary Medicine*, 4:288-293 (1998).

Schwaller, M. et al., "Reduction-reoxidation cycles contribute to catalysis of disulfide isomerization by protein-disulfide isomerase", *The Journal of Biological Chemistry*, 278(9):7154-7159 (2003).

Selman, M. et al., "Idiopathic pulmonary fibrosis: prevailing and evolving hypotheses about its pathogenesis and implications for therapy", *Ann. Intern. Med.*, 134:136-151 (2001).

Shamon, L.A. et al., "Evaluation of the mutagenic, cytotoxic, and antitumor potential of triptolide, a highly oxygenated diterpene isolated from *Tripterygium wilfordii*", *Cancer Letters*, 112:113-117 (1997).

Shanmuganathan et al., "Enhanced brain delivery of an anti-HIV nucleoside 2'-F-ara-ddl by xanthine oxidase mediated biotransformation", *J. Med. Chem.*, 37:821-827 (1994).

Shevchenko, A. et al., "Mass spectrometric sequencing of proteins silver-stained polyacrylamide gels", *Anal. Chem.*, 68(5):850-858 (1996).

Shevchenko, A. et al., "Linking genome and proteome by mass spectrometry: large-scale identification of yeast proteins from two dimensional gels", *Proc Natl Acad Sci USA*, 93:14440-14445 (1996).

Show, M. et al., "Reduced intratesticular testosterone concentration alters the polymerization state of the Sertoli cell intermediate filament cytoskeleton by degradation of vimentin", *Endocrinology*, 144(12):5530-6 (2003).

Solit, D. et al., "Hsp90 as a therapeutic target in prostate cancer", *Seminars in Oncology*, 30(5):709-16 (2003).

Sontag et al., "Protein phosphatase 2A is a critical regulator of protein kinase C zeta signaling targeted by SV40 small t to promote cell growth and NF-kappaB activation", *The EMBO Journal*, 16(18):5662-5671 (1997).

Stella, V.J. et al., "Prodrugs, Do they have advantages in Clinical Practice ?", *Drugs*, 29:455-473 (1985).

Tolstonog et al., "Role of the intermediate filament protein vimentin in delaying senescence and in the spontaneous immortalization of mouse embryo fibroblasts", *DNA and Cell Biology*, 20(9):509-29(2001).

Van Tamelen et al., "Biogenetic-type total synthesis of (t, −)-triptonide and (.+ −.) -triptolide", STN International Database, CAPLUS database Document No. 96:143107 2 pages (1982).

Vierling et al., "Highly fluorinated amphiphiles as drug and gene carrier and delivery systems", *Journal of Fluorine Chemistry*, 107:337-354 (2001).

Waller, D.G. and George, C.F., "Prodrugs", *Br. J. Clin. Pharmac.*, 28:497-507 (1989).

Wahlgren, C-F. et al, "Itch and inflammation induced by intradermally injected interleukin-2 in atopic dermatitis patients and healthy subjects", *Arch Dermatol Res.*, 287(6):572-580 (1995).

Wang, Z. et al., "Altered distribution of Sertoli cell vimentin and increased apoptosis in cryptorchid rats", *Journal of Pediatric Surgery*, 37(4):648-652 (2002).

Wang, J. et al., "Immunosuppressive activity of the Chinese medicinal plant *Tripterygium wilfordii*. I. Prolongation of rat cardiac and renal allograft survival by the PG27 extract and immunosuppressive synergy in combination therapy with cyclosporine", *Transplantation*, 70(3):447-455 (2000).

Wang, J. and Morris, R.E., "Effect of splenectomy and mono- or combination therapy with rapamycin, the morpholinoethyl ester of mycophenolic acid and deoxyspergualin on cardiac xenograft survival", *Transplantation Proceedings*, 23(1):699-702 (1991).

Wang, X. et al., "Mechanism of triptolide-induced apoptosis: Effect on caspase activation and Bid cleavage and essentiality of the hydroxyl group of triptolide", *J. Mol. Med.*, 84:405-415 (2006).

Weng, G. et al. "Advances in studies on apoptosis induced by *Tripterygium wilfordii*", *Chinese Traditional and Herbal Drugs*, 33(11):1053-1054 (2002) (No English Abstract Translation).

Whitesell, L. et al., "The stress response: implications for the clinical development of hsp90 inhibitors", *Current Cancer Drug Targets*, 3(5):349-358 (2003).

Yamagishi, S. et al., "Advanced glycation end products inhibit de novo protein synthesis and induce TGF-beta overexpression in proximal tubular cells", *Kidney International*, 63(2):464-473 (2003).

Yamamoto, R. et al., "Pharmaceutical Studies on water-Soluble corticosteroid derivatives I. Stability of Hydrocortisone 21 Hemiesters in Solution", Journal of the Pharmaceutical Society of Japan, 46(8):855-862 (1971).

Yang, S. et al., "Triptolide Induces apoptotic death of T lymphocyte", *Immunopharmacology*, 40:139-149 (1998).

Yang, J. et al., "Disruption of the EF-2 kinase/Hsp90 protein complex: a possible mechanism to inhibit glioblastoma by geldanamycin", *Cancer Research*, 61(10):4010-4016 (2001).

Yang, S. et al., "Triptolide Inhibits the Growth and Metastasis of Solid Tumors", *Molecular Cancer Therapeutics*, 2:65-72 (2003).

Yano, H. et al., "Inhibition of histamine secretion by wortmannin through the blockade of phosphatidylinositol 3-kinase in RBL-2H3 cells", *The Journal of Biological Chemistry*, 268(34):25846-25856 (1993).

Yuan, G-H. et al., "Characterization of cells from pannus-like tissue over articular cartilage of advanced osteoarthritis", *OsteoArthritis and Cartilage*, 12(1):38-45 (2004).

Zhang et al., "Studies on Diterpenoids from leaves of *Triptetygium wilfordii*", ACTA Pharmaceutica Sinica, 28(2):110-115 (1993). (English Abstract translation).

Zheng et al., "Screening of active iantiinflammatory, immunosuppressive and antifertility components of *Tripterygium wilfordii*", Chemiacl Abstracts 117(9): Abstract No. 83085a (1992).

Zhou, H-F. et al., "Triptolide inhibits TNF-alpha, IL-1 beta and NO production in primary microglial cultures", *Neuroreport*, 14(7):1091-5 (2003).

Zhou, Y.X. et al., *Ai Zheng 21*:1108-8 (2002).

Anderson, Wayne K. et al., "Synthesis, Evaluation of Chemical Reactivity, and Murine Antineoplastic Activity of 2-Hydroxy-5-(3,4-dichlorophenyl)-6,7-bis(hydroxymethyl)-2,3-dihydro-1*H*-pyrrolizine Bis(2-propylcarbamate) and 2-Acyloxy Derivatives as Potential Water-Soluble Prodrugs[1]", *J. Med. Chem.*, 26:1333-1338 (1983).

International Search Report in PCT Application No. PCT/US03/17177, search report dated Mar. 24, 2004, 3 pages (2004).

Dan et al., "Studies on triepoxide analogs of triptolide", *Tetrahedron Letters*, 38(39):6865-6868(1997).

de Groot Franciscus M. H. et al., "Synthesis and Biological Evaluation of 2'-Carbamate-Linked and 2'-Carbonate-Linked Prodrugs of Paclitaxel: Selective Activation by the Tumor-Associated Protease Plasmin", *J. Med. Chem.*, 43:3093-3102 (2000).

De Quan Yu et al., "Chemical Transformation of Triptolide", *Chinese Chemical Letters*, 2(12):937-940 (1991).

Dittert, L.W. et al., "Acetaminophen Prodrugs I Synthesis, Physicochemical Properties, and Analgesic Activity", *Journal of Pharmaceutical Sciences*, 57(5):774-780 (1968).

Dittert, L.W. et al., "Acetaminophen Prodrugs II Effect of Structure and Enzyme Source on Enzymatic and Nonenzymatic Hydrolysis of Carbonate Esters", *Journal of Pharmaceutical Sciences*, 57(5):780-783 (1968).

Hansen, Kristian T. et al., "Carbamate Ester Prodrus of Dopaminergic Compounds: Synthesis, Stability, and Bioconversion", *Journal of Pharmaceutical Sciences*, 80(8):793-798, 1991.

Hansen, Laila B. et al., "Ketobemidone prodrugs for buccal delivery", *Acta Pharm. Nord.*, 3(2):77-82, 1991.

Huang, Tien L. etal., "Hydrolysis of Carbonates, Thiocarbonates, Carbamates, and Carboxylic Esters of α-Naphthol, β-Naphthol, and *p*-Nitrophenol by Human, Rat, and Mouse Liver Carboxylesterases", *Pharmaceutical Research*, 10(5):639-648, 1993.

Kahns Anne M. et al., "Prodrugs of Peptides. 18. Synthesis and Evaluation of Various Esters of Desmopressin (dDAVP)", *Pharmaceutical Research*, 10(1):68-74 (1993).

Nassar, Munir N. et al., "Effects of Structural Variations on the Rates of Enzymatic and Nonenzymatic Hydrolysis of Carbonate and Carbamate Esters", *Journal of Pharmaceutical Sciences*, 81(3):295-298 (1992).

Savolainen, Jouko et al., "Synthesis and in vitroIn vivo evaluation of novel oral *N*-alkyl- and *N,N*-dialkyl-carbamate esters of entacapone", *Life Sciences*, 67:205-216 (2000).

Tunek, Anders et al., "Hydrolysis of [3]H-Bambuterol, A Carbamate Prodrug of Terbutaline, in Blood from Humans and Laboratory Animals In Vitro", *Biochemical Pharmacology*, 37(20):3867-3876 (1988).

Weibel, Helle et al., "Macromolecular prodrugs IXX. Kinetics of hydrolysis of benzyl dextran carbonate ester conjugates in aqueous buffer solutions and human plasma", *Acta Pharm. Nord.*, 3(3):159-162 (1991).

Chen, J-Y et al., "Improved Preparation of Triptolide Extract", *Chinese Journal of Pharmaceutcials*, 20(5):195 and 200 (Dec. 31, 1989) (English translation of abstract and concise explanation of relevance from Foreign Office Action).

Textbook of Chinese Medicine Chemistry for Chinese Colleges of Traditional Chinese Medicine in the New Century (for Chinese Medicine Specialty), Kuang Hai-Xue p. 23, Chinese Press of Traditional Chinese Medicine (Jun. 30, 2003) (English translation of abstract and concise explanation of relevance from Foreign Office Action).

* cited by examiner

US 7,662,976 B2

TRIPTOLIDE DERIVATIVES FOR MODULATION OF APOPTOSIS AND IMMUNOSUPPRESSION

CROSS-REFERENCE TO RELATED APPLICATIONS

This application is a divisional application of currently pending U.S. application Ser. No. 10/478,777, filed Jun. 24, 2004 a 35 U.S.C. § 371 National Stage of International Application No. PCT/US03/17177, filed 29 May 2003, which claims the benefit under 35 U.S.C. § 119(e) of Provisional Application No. 60/384,480, filed 31 May 2002, the contents of each of which are expressly incorporated herein by reference.

FIELD OF THE INVENTION

The present invention relates to prodrugs useful as immunosuppressive, anti-inflammatory and anticancer agents, and methods of their use. The compounds have good aqueous solubility and convert to biologically active compounds in vivo, at a rate which can be modulated by varying the substitution on the prodrug.

REFERENCES

Bagshawe, K. D. Antibody directed enzymes revive anticancer prodrugs concept. *Br J Cancer* 56:531-532 (1987).

Bagshawe, K. D. Antibody-directed enzyme prodrug therapy (ADEPT). *Adv Pharmacol.* 24:99-121 (1993).

Bagshawe, K. D, Springer, C. J., Searle, F., Antoniw, P., Sharma, S. K., Melton, R. G., Sherwood R F. A cytotoxic agent can be generated selectively at cancer sites. *Br J Cancer* 58:700-703 (1988).

Bagshawe, K. D. Towards generating cytotoxic agents at cancer sites. *Br J Cancer* 60:275-281 (1989).

Boyd, G. V. and Heatherington, K., *J. Chem. Soc. Perkin I* 2523-2531 (1973).

Ferrier, R. J., in *CARBOHYDRATE CHEMISTRY*, Kennedy, J. F., Ed., Clarendon Press, Oxford (1990).

Garver, L. C. et al., *J. Am. Chem. Soc.* 104:867 (1982).

Gleichmann, E. et al., *Immunol. Today* 5:324 (1984).

Hormi, O. E. O. and Nasman, J. H., *Syn. Commun.* 16:69 (1986).

Kocienski, P. J., *PROTECTING GROUPS*, Georg Thieme Verlag, Stuttgart (1994).

Korngold, R. and Sprent, J., *J. Exp. Med.* 148:1687 (1978).

Kupchan, S. M. et al., *J. Am. Chem. Soc.* 94:7194 (1972).

Kupchan, S. M. et al., U.S. Pat. No. 3,005,108 (1977).

Lipsky, P. E. et al., U.S. Pat. No. 5,294,443 (1994).

Ma, P-C. et al., *J. Chin. Pharm. Sci.* 1:12 (1992).

Mori, S. et al., *Tetrahedron* 47(27):5051-5070 (1991).

Morris, R. E., *Transplant Proc.* 23(6):2722-2724 (1991).

Morris, R. E. et al., *Transplant Proc.* 23(1):238-240 (1991).

Murase, N. et al., *Transplantation* 55:701 (1993).

Ono and Lindsey, *J. Thor. Cardiovasc. Surg.* 57(2):225-29 (1969).

Pu, L. et al., *Zhongguo Yaoli Xuebao* 11:76 (1990).

Wang, J. and Morris, R. E., *Transplantation Proc.* 23:699 (1991).

Wentworth. P., Datta, A., Blakey, D., Boyle, T., Partridge, L. J., Blackburn, G. M. *Proc. Natl. Acad. Sci. USA* 93:799-803 (1996).

Yu et al., *Acta Pharmaceutica Sinica* 27(11):830-836 (1992).

Zheng, J. et al., *Zhongguo Yixue Kexueyuan Xuebao* 13:391 (1991).

Zheng, J. et al., *Zhongguo Yixue Kexueyuan Xuebao* 16:24 (1994).

BACKGROUND OF THE INVENTION

Immunosuppressive agents are widely used in the treatment of autoimmune disease and in treating or preventing transplantation rejection, including the treatment of graft-versus-host disease (GVHD), a condition in which transplanted marrow cells attack the recipient's cells. Common immunosuppressive agents include azathioprine, corticosteroids, cyclophosphamide, methotrexate, 6-mercaptopurine, vincristine, and cyclosporin A. In general, none of these drugs are completely effective, and most are limited by severe toxicity. For example, cyclosporin A, a widely used agent, is significantly toxic to the kidney. In addition, doses needed for effective treatment may increase the patient's susceptibility to infection by a variety of opportunistic invaders.

A number of compounds derived from the Chinese medicinal plant *Tripterygium wilfordii* (TW) have been identified as having immunosuppressive activity, e.g. in the treatment of autoimmune disease, and in treating or preventing transplantation rejection, including the treatment of graft-versus-host disease (GVHD), a condition in which transplanted marrow cells attack the recipient's cells. See, for example, coowned U.S. Pat. No. 6,150,539 (Triptolide prodrugs having high aqueous solubility), U.S. Pat. No. 5,962,516 (Immunosuppressive compounds and methods), U.S. Pat. No. 5,843,452 (Immunotherapy composition and method), U.S. Pat. No. 5,759,550 (Method for suppressing xenograft rejection), U.S. Pat. No. 5,663,335 (Immunosuppressive compounds and methods), and U.S. Pat. No. 5,648,376 (Immunosuppressant diterpene compound), all of which are incorporated herein by reference, and references cited therein. Such compounds have also been reported to show anticancer activity. See, for example, Kupchan et al., 1972, 1977, cited above, as well as co-owned PCT Publication No. WO 02/56835, which is incorporated herein by reference.

The administration and therapeutic effectiveness of these compounds have been limited, however, by their low water solubility. This problem has been addressed by formulating the compounds in mixtures of ethanol and polyethoxylated castor oil (e.g., "CREMOPHOR EL™"), allowing subsequent dilution in saline for intravenous administration. However, such formulations have suffered from high toxicity, due to the high concentration of solubilizing agent required to dissolve these compounds. For example, the ratio of solubilizing agent (ethanol plus "CREMOPHOR EL™") to triptolide in such formulations is typically on the order of 1000:1 or greater, due to the poor solubility of triptolide (Morris, 1991; Morris et al., 1991). Standardization of dosage amounts is also more problematic with a suspension than with a solution.

It is therefore desirable to provide immunosuppressive compounds having comparatively low toxicity and improved water solubility. It is also desirable to provide prodrug compounds which are convertible to an immunosuppressive form in vivo at a rate which can be controlled by selection of substituents on the prodrug.

SUMMARY OF THE INVENTION

In one aspect, the invention provides a method of inducing cell death, as in treatment of cancer, particularly in treatment of treatment of colon cancer, breast cancer, lung cancer, or prostate cancer. In another aspect, the invention provides a method of effecting immunosuppression, as in inhibition of transplant rejection, prevention or treatment of graft-versus-host disease, or treatment of an autoimmune disease. In accordance with the invention, a subject in need of such treatment is treated with an effective amount of a triptolide prodrug, or a pharmaceutically acceptable salt thereof, having the structure I, below, in a pharmaceutically acceptable vehicle.

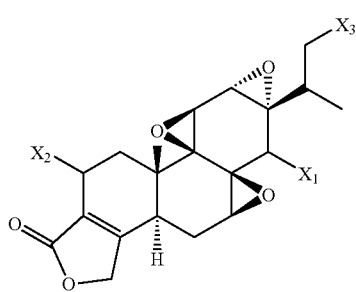

I

In the structure I, the variables are defined as follows:

$X^1$ is OH or $OR^1$, and $X^2$ and $X^3$ are independently OH, $OR^1$ or H, with the proviso that at least one of $X^1$, $X^2$ and $X^3$ is $OR^1$, and at least one of $X^2$ and $X^3$ is H; and $OR^1$ is O—(C=O)-Z, where Z is selected from the group consisting of: —$OR^2$, —O—Y—(C=O)—$OR^3$, —O—Y—$NR^4R^5$, —$NR^4R^5$, —$NR^3$—Y—(C=O)—$OR^3$, and —$NR^3$—Y—$NR^4N^5$;

wherein

Y is a divalent alkyl, alkenyl or alkynyl group having up to six carbon atoms;

$R^2$ is selected from alkyl, alkenyl, alkynyl, cycloalkyl, cycloalkenyl, aryl, aralkyl, hydroxyalkyl, alkoxyalkyl, aryloxyalkyl, and acyloxyalkyl;

each $R^3$ is independently selected from hydrogen and $R^2$; and $R^4$ and $R^5$ are independently selected from hydrogen, alkyl, alkenyl, alkynyl, cycloalkyl, cycloalkenyl, aryl, aralkyl, hydroxyalkyl, alkoxyalkyl, aryloxyalkyl, and acyloxyalkyl, or $R^4$ and $R^5$ taken together form a 5- to 7-member heterocyclic ring whose ring atoms are selected from the group consisting of carbon, nitrogen, oxygen and sulfur, wherein the ring atoms include at most 3 heteroatoms.

The groups defined as $R^2$, $R^3$, $R^4$, and $R^5$, when selected from alkyl, alkenyl, and alkynyl, preferably have up to six carbon atoms. When selected from cycloalkyl or cycloalkenyl, they preferably have 3 to 7, or, for cycloalkenyl, 5 to 7 carbon atoms. When selected from aralkyl, hydroxyalkyl, alkoxyalkyl, aryloxyalkyl, and acyloxyalkyl, the alkyl components of these groups preferably have up to six carbon atoms. In one embodiment, each of these groups is independently selected from alkyl, aryl, aralkyl, and alkoxyalkyl.

In selected embodiments, $X^2$=$X^3$=H, and Y is —$CH_2$— or —$CH_2CH_2$—. In further embodiments, $OR^1$ is selected from the group consisting of O—(C=O)—$OR^2$, O—(C=O)—O—Y—(C=O)—$OR^3$, and O—(C=O)—O—Y—$NR^4R^5$ (carbonate derivatives). In other embodiments, $OR^1$ is -selected from the group consisting of O—(C=O)—$NR^4R^5$, O—(C=O)—$NR^3$—Y—(C=O)—$OR^3$, and O—(C=O)—$NR^3$—Y—$NR^4N^5$ (carbamate derivatives).

These and other objects and features of the invention will become more fully apparent when the following detailed description of the invention is read in conjunction with the accompanying drawings.

DETAILED DESCRIPTION OF THE INVENTION

I. Definitions

Figure 1:
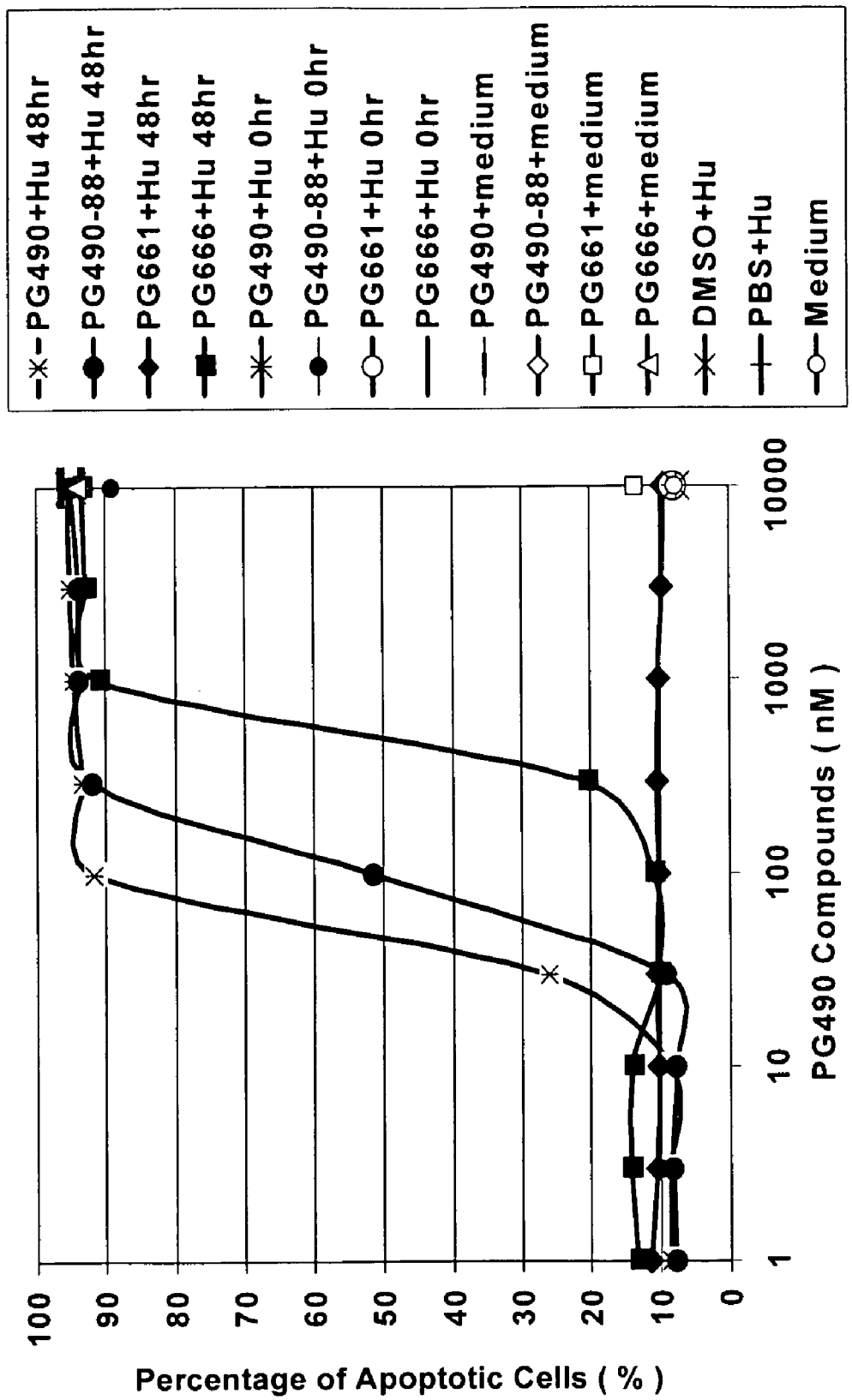
FIG. 1 is a graph showing apoptosis induction by invention compound PG666 (14-ethyl carbamate), in comparison to triptolide (PG490), its 14-succinyl ester (PG490-88), and its 14-glutamyl ester (PG661); see also Table 3.

The terms below have the following meanings unless indicated otherwise.

"Triptolide derivatives" or "triptolide analogs" refers to derivatives of triptolide, 16-hydroxytriptolide, or tripdiolide (2-hydroxytriptolide) which are derivatized at one or more hydroxyl groups.

"Alkyl" refers to a fully saturated acyclic moiety consisting of carbon and hydrogen, which may be linear or branched. Examples of alkyl groups are methyl, ethyl, n-butyl, t-butyl, n-heptyl, and isopropyl. Generally preferred are lower alkyl groups, having one to six carbon atoms, as exemplified by methyl, ethyl, n-butyl, i-butyl, t-butyl, isoamyl, n-pentyl, and isopentyl.

"Cycloalkyl" refers to a fully saturated cyclic moiety consisting of carbon and hydrogen, having three to eight carbon atoms, preferably three to six carbons atoms; e.g. cyclopropyl or methylcyclopentyl. "Cycloalkenyl" refers to an unsaturated cyclic moiety consisting of carbon and hydrogen, having five to eight carbon atoms, preferably five or six carbon atoms.

"Alkenyl" refers to an unsaturated acyclic moiety consisting of carbon and hydrogen, which may be linear or branched, having one or more double bonds. Generally preferred are lower alkenyl groups, having two to six carbon atoms. "Alkynyl" refers to an unsaturated acyclic moiety consisting of carbon and hydrogen, which may be linear or branched, containing one or more triple bonds. Generally preferred are lower alkynyl groups, having two to six carbon atoms.

"Aryl" refers to a substituted or unsubstituted monovalent aromatic radical, generally having a single ring (e.g., benzene) or two condensed rings (e.g., naphthyl), where monocyclic aryl groups are preferred. The term includes heteroaryl groups, which are aromatic ring groups having one or more nitrogen, oxygen, or sulfur atoms in the ring, such as furyl, pyrrole, pyridyl, and indole. By "substituted" is meant that one or more ring hydrogens in the aryl group, preferably one or two ring hydrogens, is replaced with a group preferably selected from fluorine, chlorine, bromine, methyl, ethyl, hydroxy, hydroxymethyl, nitro, amino, methylamino, dimethylamino, methoxy, halomethoxy, and halomethyl.

"Acyloxyalkyl" refers to a substituent of the form —R—O—(C=O)—R', where R is alkyl, preferably having up to six carbon atoms, and R' is selected from alkyl, alkenyl, alkynyl, aryl, and aralkyl, where R' preferably comprises lower alkyl, lower alkenyl, or lower alkynyl (i.e. $C_2$-$C_6$) groups and monocyclic aryl groups.

"Aralkyl" refers to an alkyl, preferably lower ($C_1$-$C_4$, more preferably $C_1$-$C_2$) alkyl, substituent which is further substituted with an aryl group, preferably a monocyclic aryl group; examples are benzyl and phenethyl. Also included is fluorenylmethyl, a component of the widely employed Fmoc (fluorenylmethoxycarbonyl) protecting group.

The term "pharmaceutically acceptable salt" encompasses carboxylate salts having organic and inorganic cations, such as alkali and alkaline earth metal cations (for example, lithium, sodium, potassium, magnesium, barium and calcium); ammonium; or organic cations, for example, dibenzylammonium, benzylammonium, 2-hydroxyethylammonium, bis(2-hydroxyethyl) ammonium, phenylethylbenzylammonium, dibenzylethylene diammonium, and the like. Other cations encompassed by the above term include the protonated form of procaine, quinine and N-methylglucosamine, and the protonated forms of basic amino acids such as glycine, ornithine, histidine, phenylglycine, lysine, and arginine.

The term also includes salts formed by standard acid-base reactions with basic groups, such as amino groups, having a counterion derived from an organic or inorganic acid. Such counterions include chloride, sulfate, phosphate, acetate, succinate, citrate, lactate, maleate, fumarate, palmitate, cholate, glutamate, glutarate, tartrate, stearate, salicylate, methanesulfonate, benzenesulfonate, sorbate, picrate, benzoate, cinnamate, and the like.

For the purposes of the current disclosure, the following numbering scheme is used for triptolide and triptolide analogs:

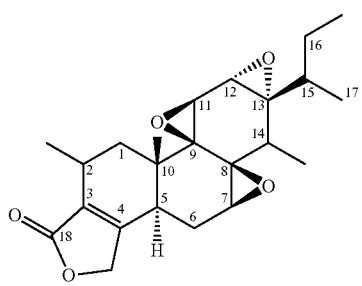

II. Triptolide Analogs

Compounds as represented by structure I, below, are derivatives of triptolide having hydrophilic substituents, possess greater water solubility than the non-derivatized starting compound, and are effective to hydrolyze and convert in vivo to the parent compound. The compounds are useful as prodrugs for immunosuppressive, anti-inflammatory and anticancer applications.

A. Structure

In compounds of formula I:

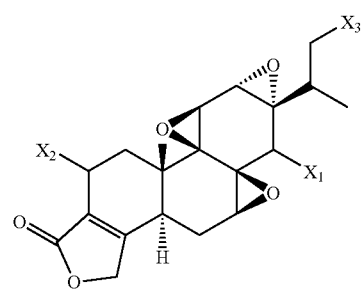

$X^1$ is OH or $OR^1$, and $X^2$ and $X^3$ are independently OH, $OR^1$ or hydrogen, with the proviso that at least one of $X^1$, $X^2$ and $X^3$ is $OR^1$, and at least one of $X^2$ and $X^3$ is hydrogen.

$OR^1$ is a carbamate or carbonate group, which may be further substituted, e.g. with an ester or amine. In particular, where $OR^1$ is represented as O—(C=O)-Z, Z is selected from the group consisting of:
—$OR^2$,
—O—Y—(C=O)—$OR^3$,
—O—Y—$NR^4R^5$,
—$NR^4R^5$,
—$NR^3$—Y—(C=O)—$OR^3$ and
—N—Y—$NR^4N5$, where Y is a divalent alkyl, alkenyl or alkynyl group having up to six carbon atoms; $R^2$ is selected from alkyl, alkenyl, alkynyl, cycloalkyl, cycloalkenyl, aryl, aralkyl, hydroxyalkyl, alkoxyalkyl, aryloxyalkyl, and acyloxyalkyl; and each $R^3$ is independently selected from hydrogen and $R^2$. $R^4$ and $R^5$ are independently selected from hydrogen, alkyl, alkenyl, alkynyl, cycloalkyl, cycloalkenyl, aryl, aralkyl, hydroxyalkyl, alkoxyalkyl, aryloxyalkyl, and acyloxyalkyl. Alternatively, $R^4$ and $R^5$ taken together may form a 5- to 7-member heterocyclic ring whose ring atoms are selected from the group consisting of carbon, nitrogen, oxygen and sulfur, where the ring atoms include at most 3 heteroatoms. Examples include, but are not limited to, piperidine, piperazine, pyrrolidine, and morpholine.

The groups defined as $R^2$, $R^3$, $R^4$, and $R^5$, when selected from alkyl, alkenyl, and alkynyl, preferably have up to six carbon atoms. When selected from cycloalkyl or cycloalkenyl, they preferably have 3 to 7, or, for cycloalkenyl, 5 to 7 carbon atoms. When selected from aralkyl, hydroxyalkyl, alkoxyalkyl, aryloxyalkyl, and acyloxyalkyl, the alkyl components of these groups preferably have up to six carbon atoms. In one embodiment, each of these groups is independently selected from alkyl, aryl, aralkyl, and alkoxyalkyl.

In one embodiment, $X^1$ is $OR^1$, and each of $X^2$ and $X^3$ is hydrogen. In another embodiment, Y is methylene (—$CH_2$—) or ethylene (—$CH_2CH_2$—).

B. Preparation

The compounds of structure I may be prepared from triptolide, as obtained from the root xylem of the Chinese medicinal plant *Tripterygium wilfordii* (TW) or from other known sources. The TW plant is found in the Fujiang Province and other southern provinces of China; TW plant material can generally be obtained in China or through commercial sources in the United States. Methods for preparing triptolide and some of its derivatives (e.g. tripdiolide and 16-hydroxytriptolide) are known in the art and are described, for example, in Kupchan et al. (1972, 1977); Lipsky et al. (1994); Pu et al. (1990); and Ma et al. (1992).

The hydroxyl group(s) of triptolide or its derivatives can be converted to the carbamates of structure I by reaction with an appropriately substituted isocyanate, as shown in Examples 1 (General Procedure A), 5 and 6, or by reaction with phosgene and an appropriately substituted amine, as shown in Examples 2 (General Procedure B) and 7.

Similarly, the hydroxyl group(s) of triptolide or its derivatives can be converted to the carbonates of structure I by reaction with an appropriately substituted chloroformate, as shown in Examples 3 (General Procedure C), 8 and 9, or by reaction with phosgene and an appropriately substituted alcohol, as shown in Examples 4 (General Procedure D), 10-13 and 15. As shown in Examples 7 and 11-15, further functionality on a carbonate or carbamate alkyl group can be incorporated. Metal salts and amine salts are readily prepared by reaction or exchange with an appropriate counterion (Examples 14, 16, 17).

In cases where all available hydroxyl groups on the starting material are to be derivatized, an excess of reagent can be used to drive the reaction to completion. The compound 16-hydroxytriptolide contains two free hydroxyl groups, one secondary (at C-14) and one primary (at C-16). Since the hydroxyl group at the 16-position is more reactive than the 14-hydroxyl group for steric reasons, mono- and diester derivatives can be selectively made using appropriate reaction conditions. Reaction with a stoichiometric amount of a selected reagent yields primarily the compound monoderivatized at the 16-position, with the 14-hydroxyl group remaining free. Monoderivatives substituted at the more hindered (secondary) hydroxyl group can be prepared by first selectively protecting the less hindered (primary) hydroxyl group, carrying out the derivatization at the unprotected position, and then removing the protecting group. Suitable hydroxyl protecting groups are well known, and are described, for example, by Kocienski (1994).

Various compounds of the invention, prepared as described above and in the Examples, are given in the Table below. All are substituted at the 14-hydroxyl of triptolide with a carbonate or carbamate substituent. Also included are reference ester substituted compounds, PC490-88 and PG661, as well as the parent compound, designated herein as PG490.

TABLE 1

Exemplary Carbamate- and Carbonate-Substituted Triptolide Derivatives

| Designation | Name (Triptolide derivative) | 14-O—(C=O)X substituent |
|---|---|---|
| Controls | | |
| PG490 | Triptolide | |
| PG490-88 | 14-succinyl ester | $CH_2CH_2COOH$ |
| PG661 | 14-isoglutamyl ester | $CH_2CH_2CH(NH_2)COOH$ |
| Compounds | | |
| PG666 | 14-ethyl carbamate | $NHCH_2CH_3$ |
| PG671 | 14-phenyl carbamate | $NH(C_6H_5)$ |
| PG672 | N-methylpiperazinecarbonyl (carbamate) | 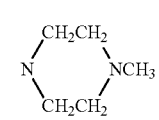 |
| PG674 | 14-ethyl carbonate | $OCH_2CH_3$ |
| PG676 | 14-phenyl carbonate | $O(C_6H_5)$ |
| PG679 | 14-ethoxyethyl carbonate | $OCH_2CH_2OCH_2CH_3$ |
| PG680 | 14-methoxycarbonylmethyl carbonate | $OCH_2(C=O)OCH_3$ |
| PG681 | 14-(R)-α-methyl-tert-butoxycarbonylmethyl carbonate | $OC^*H(CH_3)(C=O)OC(CH_3)_3$ |
| PG682 | 14-dimethylaminoethyl carbonate | $OCH_2CH_2N(CH_3)_2$ |
| PG682 PTSA | 14-dimethylaminoethyl carbonate, p-toluenesulfonate salt | $OCH_2CH_2N^+H(CH_3)_2\ {}^-OTs$ |
| PG687 | 14-hydroxycarbonylmethyl carbonate | $OCH_2COOH$ |
| PG687 Na | 14-hydroxycarbonylmethyl carbonate, sodium salt | $OCH_2COO^-\ {}^+Na$ |
| PG687 tris | 14-hydroxycarbonylmethyl carbonate, tris(hydroxymethyl)aminomethane salt | $OCH_2COO^-\ {}^+NH_3C(CH_2OH)_3$ |
| PG688 | 14-dimethylaminoethyl carbamate | $NHCH_2CH_2N(CH_3)_2$ |
| PG695 | 14-tert-butyl carbonate | $OC(CH_3)_3$ |

III. Prodrug Conversion and Apoptosis Inducing Activity

A. Conversion Assays

The compounds of formula I provide the advantage of different and sometimes widely varying rates of conversion to parent compound, as demonstrated below. Accordingly, prodrugs of formula I can be selected for different desired conversion rates in human serum/plasma by choosing different structural constituents linked via a carbonate or carbamate linkage to triptolide.

Compounds of formula I, as shown in Table 1 above and in the Examples, were assayed for their capacity to induce apoptosis in cells from the Jurkat human T lymphocyte cell line, after incubation with pooled human serum for varying periods of time at 37° C. (see Example 19). An ester prodrug, triptolide-14-succinate, designated PG490-88, was included for comparison. The extent of conversion to triptolide after such incubation was also independently determined by HPLC analysis.

The results of the apoptosis assay are presented in Table 2. The $ED_{50}$ values (column 3) are calculated directly from the data in each experiment, and the % conversion values (column 4) are calculated as percent of the $ED_{50}$ value produced by triptolide, designated PG490, incubated in the same plasma (i.e. in the same experiment). This procedure gives the most valid direct comparison of each compound to triptolide under the same experimental conditions.

Comparison of the percent conversion at each of the incubation times shows a broad range of values among the compounds. The percent conversion varied from 7% (PG681; 14-(R)-α-methyl-tert-butoxycarbonylmethyl carbonate) to 98% (PG674; 14-ethyl carbonate) after 1 hour, and from 6% (PG687-tris; 14-hydroxycarbonylmethyl carbonate, tris salt) to 100% (PG674, PG695; 14-tert-butyl carbonate) or greater (PG682; 14-dimethylaminoethyl carbonate, calculated as >100% compared to PG490) after 48 hours.

TABLE 2

| Cmpd. | Incubation Time in Serum (hours) | $ED_{50}$ (nM) in apoptosis assay after incubation with serum | Conversion, as relative $ED_{50}$ compared to triptolide (%) | $t_{1/2}$ in human plasma (min) by HPLC |
|---|---|---|---|---|
| Control | | | | |
| PG490-88 | 0.5 | 2584 | 2 | max. 26% |
| PG490-88 | 1 | 2268 | 2 | conversion |
| PG490-88 | 24 | 328 | 18 | at 48 hr (Na salt) |
| PG490-88 | 48 | 147 | 43 | |
| Compounds | | | | |
| PG674 | 0.5 | 27 | 188 | 12 |
| PG674 | 1 | 55 | 98 | |
| PG674 | 24 | 60 | 97 | |
| PG674 | 48 | 65 | 100 | |
| PG676 | 48 | 56 | 96 | 15 |
| PG679 | 0.5 | 39 | 128 | 11 |
| PG680 | 48 | 58 | 85 | 9 |
| PG681 | 1 | 684 | 7 | max. 20% |
| PG681 | 48 | 139 | 40 | conversion at 48 hr |
| PG682 | 1 | 66 | 76 | n.d. |
| PG682 | 48 | 32 | 146 | |
| PG682PTSA | 1 | 57 | 89 | 17 |
| PG687tris | 48 | 960 | 6 | max. 10% at 48 hr (Na salt) |
| PG695 | 48 | 59 | 100 | n.d. |

Prodrug conversions to triptolide as determined independently by HPLC are given in column 4. As with the bioassay data, a comparison of the $t_{1/2}$ values for conversion to triptolide shows a broad range of values among the compounds. The $t_{1/2}$ values range from 9 minutes (PG680; 14-methoxycarbonylmethyl carbonate), 11 minutes (PG679; 14-ethoxyethyl carbonate) and 12 minutes (PG674; 14-ethyl carbonate) to incomplete conversion (10%) in 48 hours of incubation (PG687Na; 14-hydroxycarbonylmethyl carbonate, sodium salt). PG681 (14-(R)-α-methyl-tert-butoxycarbonylmethyl carbonate), which exhibits the lowest percent conversion in the bioassay (7%), converts incompletely (20%) in 48 hours as assessed by HPLC. PG687 (14-hydroxycarbonylmethyl carbonate) converts only 6% within 48 hours when evaluated in the apoptosis assay, and only 10% in this time span when assayed by HPLC. PG674 (14-ethyl carbonate) converts 98% in 1 hour and 100% in 48 hours in the bioassay, and exhibits a $t_{1/2}$ of 12 minutes by HPLC analysis. PG682 (14-dimethylaminoethyl carbonate) displays conversion calculated as >100% in apoptosis induction, and a 17 minute $t_{1/2}$ by HPLC evaluation.

There is a large measure of consistency between the results of prodrug conversion in human serum to a biologically active, apoptosis-inducing compound (presumably triptolide) and the conversion in human plasma and expressed in minutes as the $t_{1/2}$ of prodrug conversion to triptolide assessed by HPLC. There is a broad range of values for the conversion of prodrugs, whether the conversion is evaluated in the apoptosis induction bioassay or by HPLC identification and quantification of triptolide. This broad range of conversion values in human serum or plasma indicates that the compounds of formula I do not share a similar conversion rate under these circumstances. This unexpected difference in conversion rates from these triptolide prodrugs to triptolide shows that different and widely varying rates of conversion can be obtained by making differently substituted prodrugs as described herein.

In general, the carbamate derivatives of the invention, as a class, were found to convert in human serum less readily than the carbonate derivatives, as a class. As discussed further below, derivatives which are resistant to hydrolysis by human esterases and proteases may be useful in antibody directed enzyme prodrug therapy.

B. Dose-Response Data

Dose-response data on apoptosis induction by invention compound PG666 (14-ethyl carbamate), in comparison to triptolide (PG490), its 14-succinyl ester (PG490-88), and its 14-glutamyl ester (PG661), is given in Table 3. The dose-response data is also represented graphically in FIG. 1.

TABLE 3

Apoptotic Induction by Triptolide Esters and Carbamate PG666 in the Presence of Human Serum

| | % apoptotic cells at given concentration (nM) | | | | | | | | |
|---|---|---|---|---|---|---|---|---|---|
| | 1 | 3 | 10 | 30 | 100 | 300 | 1000 | 3000 | 10000 |
| | Human serum, 48 hr | | | | | | | | |
| PG490 (cntrl) | 8.5 | 8.5 | 8.5 | 26.2 | 91.7 | 93.4 | 94.6 | 95.2 | 95.4 |
| PG490-88 (cntrl) | 7.8 | 8.1 | 7.8 | 9.1 | 51.5 | 92.1 | 93.9 | 94.1 | 95.1 |
| PG661 (cntrl) | 11.3 | 10.4 | 10.3 | 10.5 | 10.3 | 10.5 | 10.2 | 9.7 | 9.4 |
| PG666 | 13.4 | 14.4 | 14.0 | 10.1 | 11.0 | 20.6 | 91.0 | 92.9 | 93.5 |

TABLE 3-continued

Apoptotic Induction by Triptolide Esters and Carbamate PG666 in the Presence of Human Serum

| | % apoptotic cells at given concentration (nM) | | | | | | | | |
|---|---|---|---|---|---|---|---|---|---|
| | 1 | 3 | 10 | 30 | 100 | 300 | 1000 | 3000 | 10000 |
| Human serum, 0 hr | | | | | | | | | |
| PG490 (cntrl) | — | — | — | — | — | — | — | — | 94.9 |
| PG490-88 (cntrl) | — | — | — | — | — | — | — | — | 89.2 |
| PG661 (cntrl) | — | — | — | — | — | — | — | — | 7.9 |
| PG666 | — | — | — | — | — | — | — | — | 93.6 |
| Medium only | | | | | | | | | |
| PG490 (cntrl) | — | — | — | — | — | — | — | — | 96.5 |
| PG490-88 (cntrl) | — | — | — | — | — | — | — | — | 93.8 |
| PG661 (cntrl) | — | — | — | — | — | — | — | — | 13.6 |
| PG666 + medium | — | — | — | — | — | — | — | — | 94.3 |
| Other controls | | | | | | | | | |
| DMSO + Hu | — | — | — | — | — | — | — | — | 7.5 |
| PBS + Hu | — | — | — | — | — | — | — | — | 7.5 |
| Medium | — | — | — | — | — | — | — | — | 7.8 |

Dose-response data on apoptosis induction by invention compounds PG666 (14-ethyl carbamate), PG671 (14-phenyl carbamate) and PG 672 (N-methylpiperazinecarbonyl) (carbamate), in comparison to triptolide (PG490), its 14-succinyl ester (PG490-88), and its 14-glutamyl ester (PG661), is given in Table 4. The dose-response data is also represented graphically in FIG. 2. (Some assays gave a higher apparent background apoptosis than is usually seen, which is assumed to be an artifact isolated to this experiment.)

TABLE 4

Apoptotic Induction by Triptolide Esters and Carbamates in the Presence of Human Serum

| | % apoptotic cells at given concentration (nM) | | | | | | | | | | | |
|---|---|---|---|---|---|---|---|---|---|---|---|---|
| | 0.03 | 0.1 | 0.3 | 1 | 3 | 10 | 30 | 100 | 300 | 1000 | 3000 | 10000 |
| Serum, 48 hr | | | | | | | | | | | | |
| PG666 | 39.9 | 40.7 | 40.8 | 41.3 | 39.8 | 39.8 | 39.1 | 40.2 | 44.5 | 88.6 | 96.8 | 92.3 |
| PG671 | 42.5 | 43.3 | 43.9 | 44.2 | 43.2 | 42.4 | 44.7 | 43.5 | 43.1 | 43.0 | 43.3 | 15.4 |
| PG672 | 42.7 | 45.2 | 45.4 | 45.9 | 45.3 | 46.0 | 46.8 | 46.6 | 42.3 | 43.7 | 44.9 | 63.2 |
| Controls | | | | | | | | | | | | |
| PG490 | 7.0 | 6.9 | 6.8 | 6.4 | 7.0 | 7.1 | 29.4 | 90.9 | 93.0 | 93.2 | 94.6 | 94.2 |
| PG490-88 | 6.6 | 6.5 | 7.0 | 6.0 | 6.2 | 6.2 | 6.8 | 30.5 | 89.6 | 92.6 | 92.8 | 93.9 |
| PG661 | 38.8 | 38.2 | 39.0 | 39.2 | 39.1 | 39.2 | 40.3 | 38.6 | 36.3 | 28.7 | 28.2 | 5.2 |
| Serum, 0 hr | | | | | | | | | | | | |
| PG666 | — | — | — | — | — | — | — | — | — | — | — | 87.2 |
| PG671 | — | — | — | — | — | — | — | — | — | — | — | 10.2 |
| PG672 | — | — | — | — | — | — | — | — | — | — | — | 47.6 |
| Controls | | | | | | | | | | | | |
| PG490 | — | — | — | — | — | — | — | — | — | — | — | 92.1 |
| PG490-88 | — | — | — | — | — | — | — | — | — | — | — | 82.9 |
| PG661 | — | — | — | — | — | — | — | — | — | — | — | 5.2 |
| Medium | | | | | | | | | | | | |
| PG666 | — | — | — | — | — | — | — | — | — | — | — | 92.6 |
| PG671 | — | — | — | — | — | — | — | — | — | — | — | 13.7 |
| PG672 | — | — | — | — | — | — | — | — | — | — | — | 48.6 |
| Controls | | | | | | | | | | | | |
| PG490 | — | — | — | — | — | — | — | — | — | — | — | 93.4 |
| PG490-88 | — | — | — | — | — | — | — | — | — | — | — | 89.7 |
| PG661 | — | — | — | — | — | — | — | — | — | — | — | 7.3 |
| DMSO + Hu | — | — | — | — | — | — | — | — | — | — | — | 6.7 |
| PBS + Hu | — | — | — | — | — | — | — | — | — | — | — | 6.6 |

Figure 3:
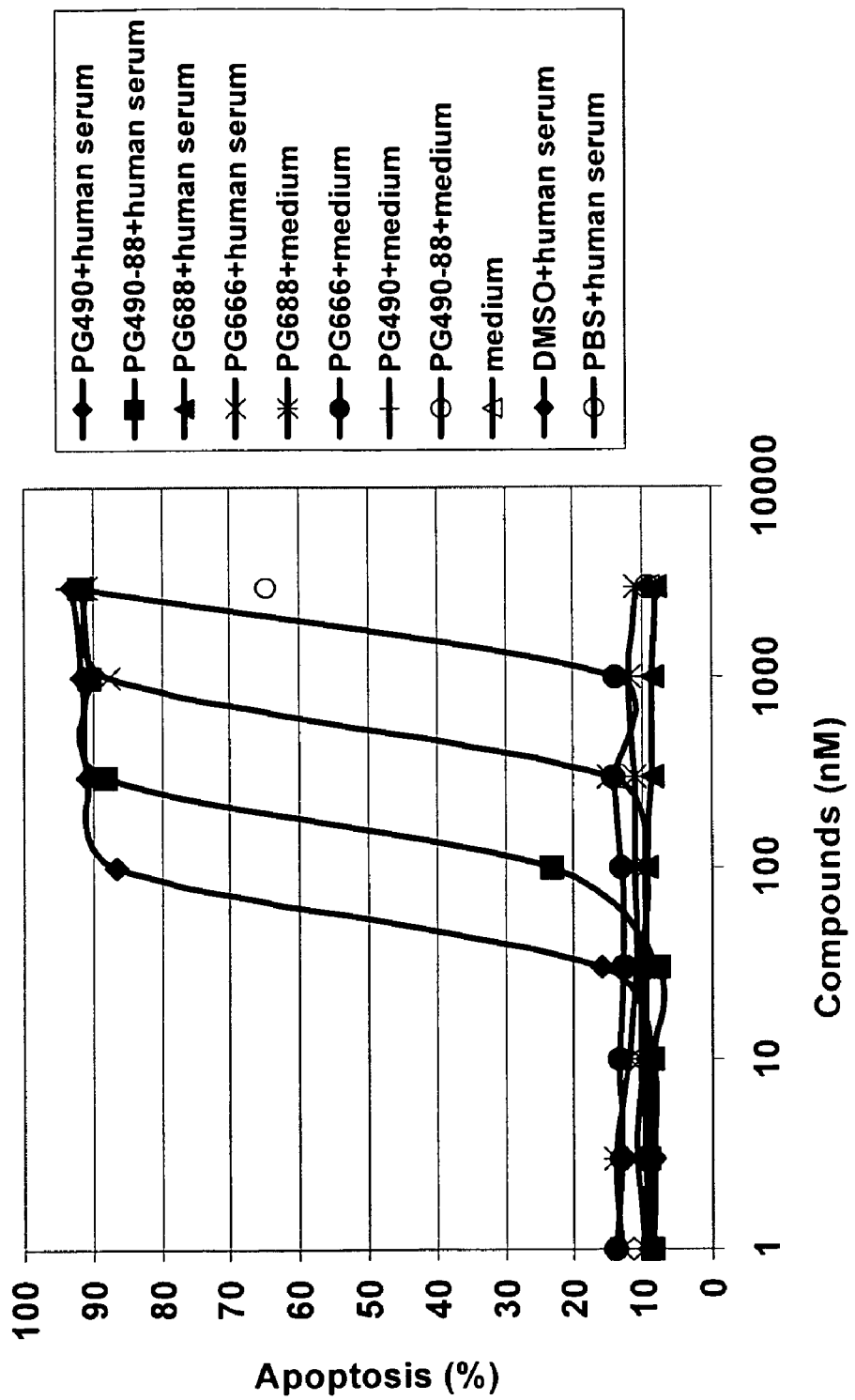
FIG. 3 is a graph showing apoptosis induction by invention compounds PG666 (14-ethyl carbamate) and PG688 (14-dimethylaminoethyl carbamate), in comparison to triptolide (PG490) and its 14-succinyl ester (PG490-88); see also Table 5.

Dose-response data on apoptosis induction by invention compounds PG666 (14-ethyl carbamate) and PG688 (14-dimethylaminoethyl carbamate), in comparison to triptolide (PG490) and its 14-succinyl ester (PG490-88), is given in Table 5. The dose-response data is also represented graphically in FIG. 3.

TABLE 5

Apoptotic Induction by Triptolide Esters and Carbamates in the Presence of Human Serum (48 hrs)

| | % apoptotic cells at given concentration (nM) | | | | | | | |
|---|---|---|---|---|---|---|---|---|
| | 1 | 3 | 10 | 30 | 100 | 300 | 1000 | 3000 |
| Human serum | | | | | | | | |
| PG490 (cntrl) | 8.8 | 8.5 | 8.6 | 15.9 | 86.5 | 90.7 | 91.7 | 93.1 |
| PG490-88 (cntrl) | 8.6 | 9.3 | 8.7 | 7.8 | 23.3 | 88.4 | 90.5 | 91.7 |
| PG688 | 9.2 | 9.8 | 9.4 | 9.5 | 9.4 | 8.7 | 8.6 | 8.2 |
| PG666 | 9.8 | 10.9 | 10.4 | 10.2 | 9.5 | 14.9 | 87.7 | 91.0 |
| Medium | | | | | | | | |
| PG490 (cntrl) | — | — | — | — | — | — | — | 93.7 |
| PG490-88 (cntrl) | — | — | — | — | — | — | — | 64.8 |
| PG688 | 13.0 | 14.0 | 12.1 | 10.9 | 11.2 | 11.3 | 12.1 | 10.9 |
| PG666 | 13.9 | 13.1 | 13.4 | 13.0 | 13.2 | 14.2 | 14.1 | 92.1 |
| Other controls | | | | | | | | |
| Medium | — | — | — | — | — | — | — | 9.1 |
| DMSO + Hu | — | — | — | — | — | — | — | 9.2 |
| PBS + Hu | — | — | — | — | — | — | — | 9.1 |

Figure 2:
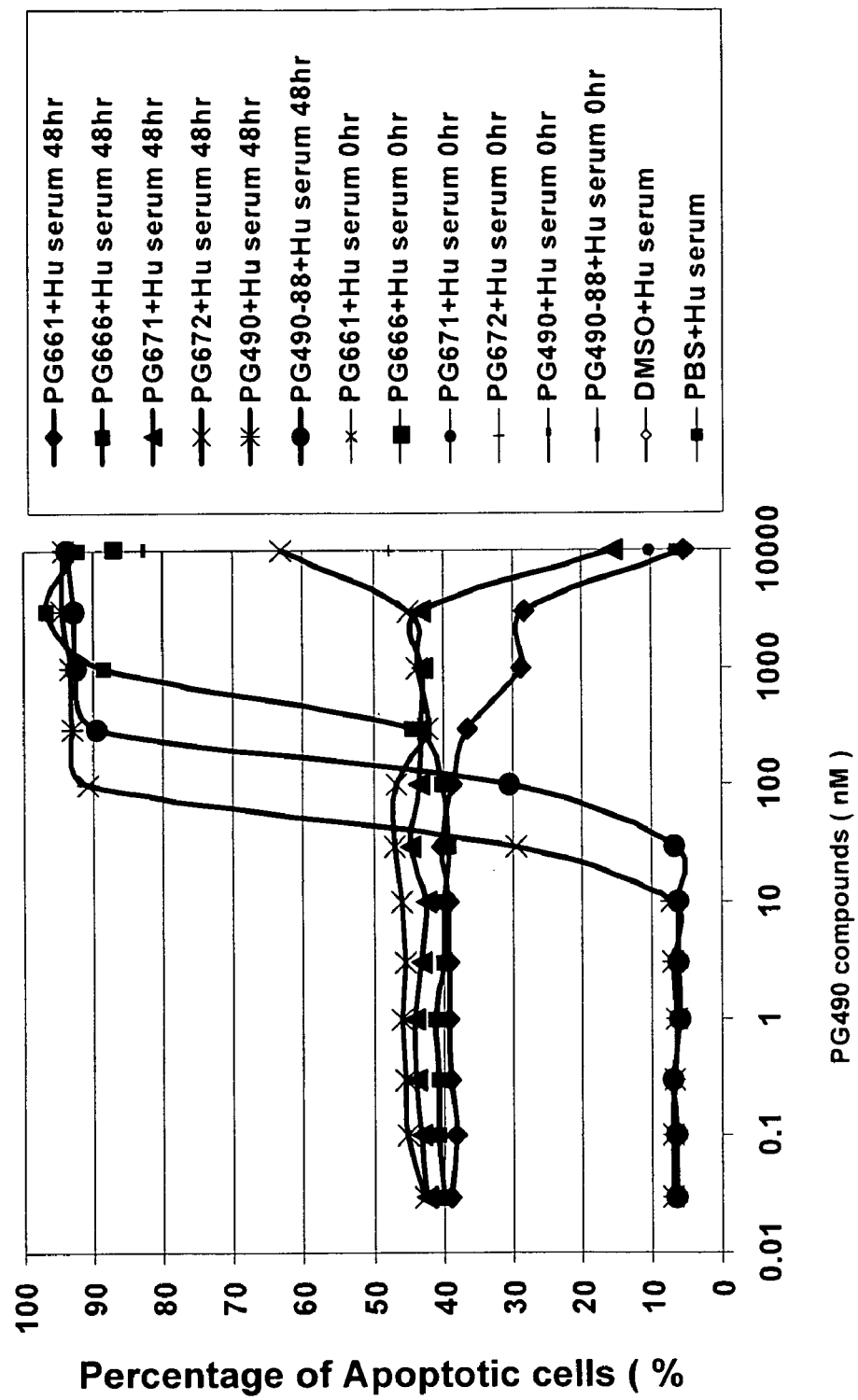
FIG. 2 is a graph showing apoptosis induction by invention compounds PG666 (14-ethyl carbamate), PG671 (14-phenyl carbamate) and PG 672 (N-methylpiperazinecarbonyl) (carbamate), in comparison to triptolide (PG490), its 14-succinyl ester (PG490-88), and its 14-glutamyl ester (PG661); see also Table 4.

Inspection of the dose-response data for these compounds shows PG666 (14-ethyl carbamate) to be more active than PG688 (4-dimethylaminoethyl carbamate) and PG671 (14-phenyl carbamate) after 48 hr. incubation in human serum. PG666 showed equal apoptotic activity to PG490 (triptolide) at roughly a 10-fold higher concentration. The N-methylpiperazinecarbamate (PG672) showed activity at high concentrations (FIG. 2), while the isoglutamyl ester (PG661) showed essentially no activity (FIGS. 1-2).

III. Anticancer Treatment

Triptolide prodrugs have shown effectiveness in cancer treatment in vivo. See, for example, coowned PCT Publication No. WO 02/56835, which is incorporated herein by reference. This document describes high efficacy of a triptolide prodrug, in comparison to 5-FU and CPT-11, in studies with tumor xenografts of the HT-29 human colon cancer cell line. The triptolide prodrug (a 14-succinate derivative of triptolide) strongly inhibited tumor growth, to a significantly greater degree than 5-FU and CPT-11, and induced tumor regression.

The invention thus includes the use of a composition as described herein to treat cancers, including cancers involving cells derived from reproductive tissue (such as Sertoli cells, germ cells, developing or more mature spermatogonia, spermatids or spermatocytes and nurse cells, germ cells and other cells of the ovary), the lymphoid or immune systems (such as Hodgkin's disease and non-Hodgkin's lymphomas), the hematopoietic system, and epithelium (such as skin and gastrointestinal tract), solid organs, the nervous system, and musculo-skeletal tissue. The triptolide prodrugs may be used for treatment of various cancer cell types, including, but not limited to, breast, colon, small cell lung, large cell lung, prostate, malignant melanoma, liver, kidney, pancreatic, esophogeal, stomach, ovarian, cervical or lymphoma tumors. Treatment of breast, colon, lung, and prostate tumors is particularly contemplated. Treatment of leukemias is also contemplated. The composition may be administered to a patient afflicted with cancer and/or leukemia by any conventional route of administration, as discussed above.

The method is useful to slow the growth of tumors, prevent tumor growth, induce partial regression of tumors, and induce complete regression of tumors, to the point of complete disappearance. The method is also useful in preventing the outgrowth of metastases derived from solid tumors.

The compositions of formula I may be administered as sole therapy or with other supportive or therapeutic treatments not designed to have anti-cancer effects in the subject. The method also includes administering the compounds of formula I in combination with one or more conventional anti-cancer drugs or biologic protein agents, where the amount of drug(s) or agent(s) is, by itself, ineffective to induce the appropriate suppression of cancer growth, in an amount effective to have the desired anti-cancer effects in the subject. Such anti-cancer drugs include actinomycin D, camptothecin, carboplatin, cisplatin, cyclophosphamide, cytosine arabinoside, daunorubicin, doxorubicin, etoposide, fludarabine, 5-fluorouracil, hydroxyurea, gemcitabine, irinotecan, methotrexate, mitomycin C, mitoxantrone, paclitaxel, taxotere, teniposide, topotecan, vinblastine, vincristine, vindesine, and vinorelbine. Anti-cancer biologic protein agents include tumor necrosis factor (TNF), TNF-related apoptosis inducing ligand (TRAIL), other TNF-related or TRAIL-related ligands and factors, interferon, interleukin-2, other interleukins, other cytokines, chemokines, and factors, antibodies to tumor-related molecules or receptors (such as anti-HER2 antibody), and agents that react with or bind to these agents (such as members of the TNF super family of receptors, other receptors, receptor antagonists, and antibodies with specificity for these agents).

IV. Prodrug Conversion and Cytokine Inhibiting Activity

A. Conversion Assays

As discussed above, the compounds of formula I provide the advantage of different and sometimes widely varying rates of conversion to parent compound. Accordingly, prodrugs of formula I can be selected for different conversion rates in human serum/plasma by choosing different structural constituents linked via a carbonate or carbamate linkage to triptolide.

Several compounds of formula I were analyzed for their capacity to inhibit IL-2 production in Jurkat human T lymphocyte cells, after incubation with pooled human serum for 48 hours at 37° C. (see Example 20). An ester prodrug, triptolide-14-succinate, designated PG490-88, was included for comparison.

The results of the immunosuppression assay are presented in Table 6. The $IC_{50}$ values (column 1) are calculated directly from the data in each experiment. The % conversion values (column 2) are calculated as the percent of the $IC_{50}$ value produced by triptolide, designated PG490, incubated in the same plasma (i.e. in the same experiment).

TABLE 6

| Compound | $IC_{50}$ (nM) | Conversion (%) |
|---|---|---|
| PG490-88 (cntrl) | 9 | 51 |
| PG682PTSA | 2 | 97 |
| PG680 | 3 | 44 |
| PG681 | 3 | 55 |
| PG676 | 6 | 84 |
| PG679 | 12 | 11 |
| PG682 | 23 | 78 |

TABLE 6-continued

| Compound | IC$_{50}$ (nM) | Conversion (%) |
|---|---|---|
| PG687tris | 29 | 6 |
| PG687 | 61 | 2 |
| PG687Na | 92 | 1 |
| PG695 | 100 | 2 |

Again, a broad range of values is shown for the conversion of the prodrugs as evaluated in the IL-2 inhibition assay. This broad range of conversion values in human serum or plasma indicates that the compounds of formula I do not share a similar conversion rate under these circumstances. This unexpected difference in conversion rates from these triptolide prodrugs to triptolide shows that different and widely varying rates of conversion can be obtained by making differently substituted prodrugs as described herein.

B. Dose-Response Data

Dose-response data on IL-2 inhibition by invention compounds PG666 (14-ethyl carbamate) and PG688 (14-dimethylaminoethyl carbamate), in comparison to triptolide (PG490) and its 14-succinyl ester (PG490-88), is given in Table 7. The dose-response data is also represented graphically in FIG. 4.

Figure 4:
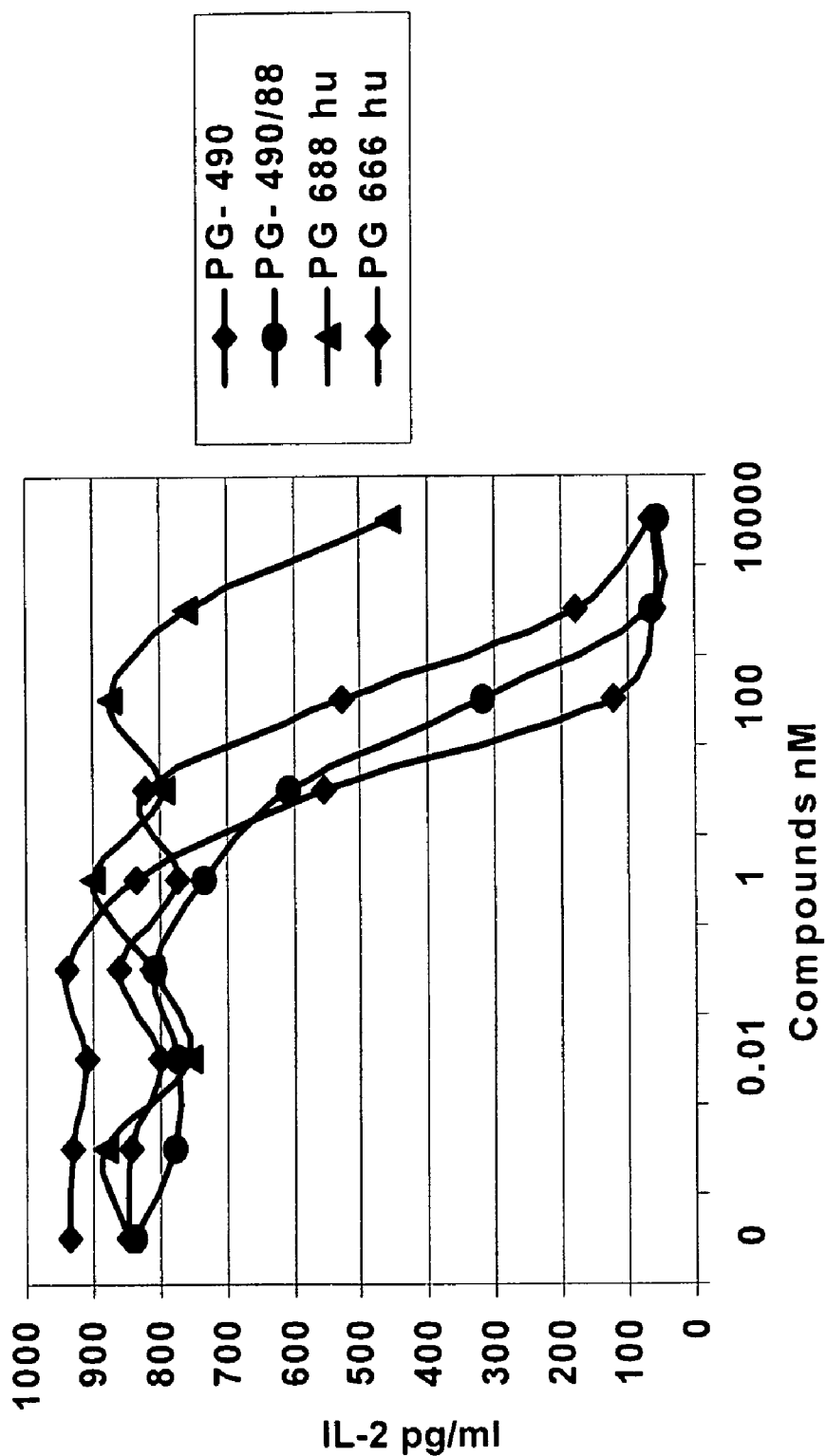
FIG. 4 is a graph showing IL-2 inhibition by invention compounds PG666 (14-ethyl carbamate) and PG688 (14-dimethylaminoethyl carbamate), in comparison to triptolide (PG490) and its 14-succinyl ester (PG490-88); see also Table 7.
Figure 5:
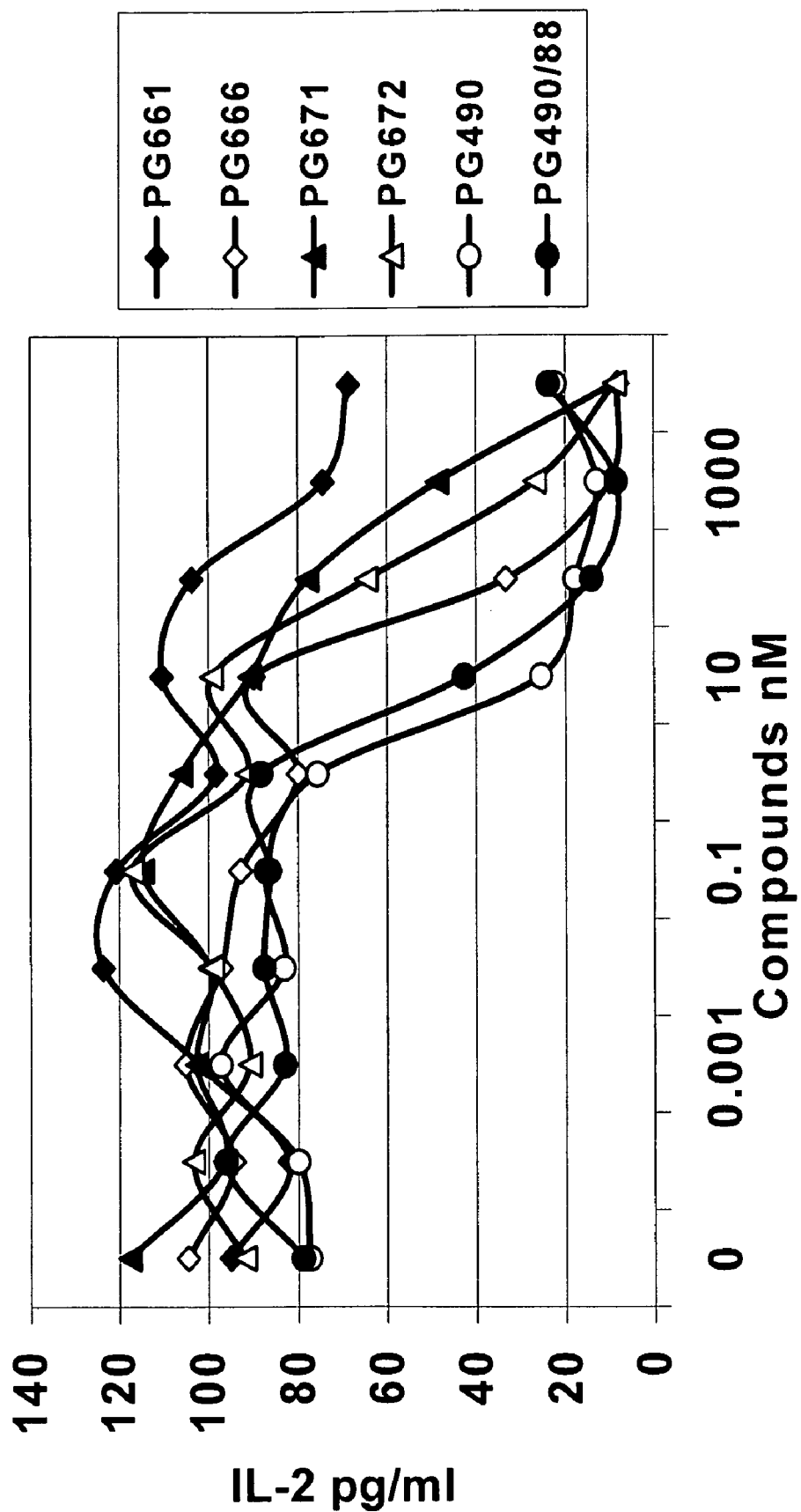
FIG. 5 is a graph showing IL-2 inhibition by invention compounds PG666 (14-ethyl carbamate), PG671 (14-phenyl carbamate) and PG672 (14-N-methylpiperazinecarbonyl) (carbamate), in comparison to triptolide (PG490), its 14-succinyl ester (PG490-88), and its isoglutamyl ester (PG661); see also Table 8.

Several of the invention compounds (PG666, 14-ethyl carbamate; PG688, 4-dimethylaminoethyl carbamate; PG671, 14-phenyl carbamate; and PG672, N-methylpiperazinecarbamate) showed some level of bioactivity in these assays (FIGS. 4-5). Again, the isoglutamyl ester (PG661) showed little or no activity (FIG. 5). PG666 (14-ethyl carbamate) showed equal IL-2 inhibitory activity to PG490 (triptolide) at about 10-30 times the active concentration of PG490.

V. Immunomodulating and Antiinflammatory Treatment

Pharmaceutical compositions comprising compounds of formula I, which are prodrugs of triptolide, are useful in other applications for which triptolide has proven effective, e.g. in immunosuppression therapy, as in treating an autoimmune disease, preventing transplantation rejection, or treating or preventing graft-versus-host disease (GVHD).

The method is useful for inhibiting rejection of a solid organ transplant, tissue graft, or cellular transplant from an incompatible human donor, thus prolonging survival and function of the transplant, and survival of the recipient. This use would include, but not be limited to, solid organ transplants (such as heart, kidney and liver), tissue grafts (such as skin, intestine, pancreas, gonad, bone, and cartilage), and cellular transplants (such as cells from pancreas, brain and nervous tissue, muscle, skin, bone, cartilage and liver).

TABLE 7

Inhibition of IL-2 production in Jurkat cells (48 hrs)

| | IL-2 pg/mL at given concentration (nM) | | | | | | | | |
|---|---|---|---|---|---|---|---|---|---|
| | 0 | 0.001 | 0.01 | 0.1 | 1 | 10 | 100 | 1000 | 10000 |
| Controls | | | | | | | | | |
| PG490 | 932.4 | 929.7 | 908.6 | 937.8 | 835.2 | 556.1 | 120.7 | 62.9 | 59.2 |
| PG490-88 | 838.0 | 776.4 | 771.0 | 809.5 | 732.4 | 605.1 | 317.5 | 65.9 | 58.2 |
| Compounds | | | | | | | | | |
| PG688, serum | 848.5 | 883.9 | 754.1 | 810.4 | 900.4 | 796.3 | 873.3 | 759.9 | 459.8 |
| PG666, serum | 846.0 | 844.6 | 799.8 | 860.6 | 773.0 | 819.1 | 528.0 | 180.1 | 63.5 |

Dose-response data on IL-2 inhibition by invention compounds PG666 (14-ethyl carbamate), PG671 (14-phenyl carbamate) and PG672 (14-N-methylpiperazinecarbonyl) (carbamate), in comparison to triptolide (PG490), its 14-succinyl ester (PG490-88), and its isoglutamyl ester (PG661), is given in Table 8. The dose-response data is also represented graphically in FIG. 5.

The method is also useful for inhibiting xenograft (interspecies) rejection; i.e. in preventing the rejection of a solid organ transplant, tissue graft, or cellular transplant from a non-human animal, whether natural in constitution or bioengineered (genetically manipulated) to express human genes, RNA, proteins, peptides or other non-native, xenogeneic molecules, or bioengineered to lack expression of the

TABLE 8

Inhibition of IL-2 production in Jurkat cells

| | IL-2 pg/mL at given concentration (nM) | | | | | | | | | |
|---|---|---|---|---|---|---|---|---|---|---|
| | 0 | 0.0001 | 0.001 | 0.01 | 0.1 | 1 | 10 | 100 | 1000 | 10000 |
| Compounds | | | | | | | | | | |
| PG666 | 104.5 | 94.3 | 105.1 | 97.0 | 92.8 | 80.0 | 89.8 | 33.3 | 10.0 | 8.0 |
| PG671 | 117.7 | 96.4 | 102.7 | 99.7 | 114.7 | 106.1 | 90.7 | 77.9 | 48.7 | 8.8 |
| PG672 | 92.0 | 103.3 | 90.8 | 99.1 | 117.1 | 91.4 | 99.1 | 64.6 | 26.8 | 8.7 |
| Controls | | | | | | | | | | |
| PG490 | 77.4 | 80.0 | 97.2 | 83.2 | 87.1 | 75.7 | 25.5 | 17.8 | 12.9 | 22.3 |
| PG490-88 | 79.0 | 96.1 | 83.0 | 87.5 | 86.3 | 88.2 | 42.7 | 14.0 | 8.4 | 23.8 |
| PG661 | 94.9 | 82.0 | 102.1 | 123.6 | 120.7 | 98.2 | 110.3 | 103.6 | 74.4 | 68.7 | animal's natural genes, RNA, proteins, peptides or other normally expressed molecules. The invention also includes the use of a composition as described above to prolong the survival of such a solid organ transplant, tissue graft, or cellular transplant from a non-human animal.

In another aspect, the invention includes a method of treatment or prevention of graft-versus-host disease, resulting from transplantation into a recipient of matched or mismatched bone marrow, spleen cells, fetal tissue, cord blood, or mobilized or otherwise harvested stem cells. The dose is preferably in the range 0.25-2 mg/kg body weight/day, preferably 0.5-1 mg/kg/day, given orally or parenterally.

Also included are methods of treatment of autoimmune diseases or diseases having autoimmune manifestations, such as Addison's disease, autoimmune hemolytic anemia, autoimmune thyroiditis, Crohn's disease, diabetes (Type I), Graves' disease, Guillain-Barre syndrome, systemic lupus erythematosus (SLE), lupus nephritis, multiple sclerosis, myasthenia gravis, psoriasis, primary biliary cirrhosis, rheumatoid arthritis and uveitis, asthma, atherosclerosis, Type I diabetes, psoriasis, and various allergies. In treating an autoimmune condition, the patient is given the composition on a periodic basis, e.g., 1-2 times per week, at a dosage level sufficient to reduce symptoms and improve patient comfort. For treating rheumatoid arthritis, in particular, the composition may be administered by intravenous injection or by direct injection into the affected joint. The patient may be treated at repeated intervals of at least 24 hours, over a several week period following the onset of symptoms of the disease in the patient.

Immunosuppressive activity of compounds in vivo can be evaluated by the use of established animal models known in the art. Such assays may be used to evaluate the relative effectiveness of immunosuppressive compounds and to estimate appropriate dosages for immunosuppressive treatment. These assays include, for example, a well-characterized rat model system for allografts, described by Ono and Lindsey (1969), in which a transplanted heart is attached to the abdominal great vessels of an allogeneic recipient animal, and the viability of the transplanted heart is gauged by the heart's ability to beat in the recipient animal. A xenograft model, in which the recipient animals are of a different species, is described by Wang (1991) and Murase (1993). A model for evaluating effectiveness against GVHD involves injection of normal $F_1$ mice with parental spleen cells; the mice develop a GVHD syndrome characterized by splenomegaly and immunosuppression (Korngold, 1978; Gleichmann, 1984). Single cell suspensions are prepared from individual spleens, and microwell cultures are established in the presence and absence of concanavalin A to assess the extent of mitogenic responsiveness.

For therapy in transplantation rejection, the method is intended particularly for the treatment of rejection of heart, kidney, liver, cellular, and bone marrow transplants, and may also be used in the treatment of GVHD. The treatment is typically initiated perioperatively, either soon before or soon after the surgical transplantation procedure, and is continued on a daily dosing regimen, for a period of at least several weeks, for treatment of acute transplantation rejection. During the treatment period, the patient may be tested periodically for immunosuppression level, e.g., by a mixed lymphocyte reaction involving allogenic lymphocytes, or by taking a biopsy of the transplanted tissue.

In addition, the composition may be administered chronically to prevent graft rejection, or in treating acute episodes of late graft rejection. As above, the dose administered is preferably 1-25 mg/kg patient body weight per day, with lower amounts being preferred for parenteral administration, and higher amounts for oral administration. The dose may be increased or decreased appropriately, depending on the response of the patient, and over the period of treatment, the ability of the patient to resist infection.

The compounds are also useful as potentiators when administered concurrently with another immunosuppressive drug for immunosuppressive treatments as discussed above. A conventional immunosuppressant drug, such as cyclosporin A, FK506, azathioprine, rapamycin, mycophenolic acid, or a glucocorticoid, may thus be administered in an amount substantially less (e.g. 20% to 50% of the standard dose) than when the compound is administered alone. Alternatively, the triptolide analog and immunosuppressive drug are administered in amounts such that the resultant immunosuppression is greater than what would be expected or obtained from the sum of the effects obtained with the drug and triptolide analog used alone. Typically, the immunosuppressive drug and potentiator are administered at regular intervals over a time period of at least 2 weeks.

The compositions of formula I are also useful for the treatment of inflammatory conditions such as asthma, both intrinsic and extrinsic manifestations. For treatment of asthma, the composition is preferably administered via inhalation, but any conventional route of administration may be useful. The composition and method may also be used for treatment of other inflammatory conditions, including traumatic inflammation, inflammation in Lyme disease, psoriasis, chronic bronchitis (chronic infective lung disease), chronic sinusitis, sepsis associated acute respiratory distress syndrome, Behcet's disease, pulmonary sarcoidosis, pemphigus, pemphigoid inflammatory bowel disease, and ulcerative colitis. Triptolide and the present analogs are also useful in reducing male fertility.

The compositions of formula I may also be administered in combination with a conventional anti-inflammatory drug (or drugs), where the drug or amount of drug administered is, by itself, ineffective to induce the appropriate suppression or inhibition of inflammation.

The dose that is administered is preferably in the range of 1-25 mg/kg patient body weight per day, with lower amounts being preferred for parenteral administration, and higher amounts being preferred for oral administration. Optimum dosages can be determined by routine experimentation according to methods known in the art.

VI. Prodrugs of Triptolide as Substrates for Antibody-conjugated Enzymes

Triptolide derivatives which are resistant to hydrolysis by human esterases and proteases may be advantageously employed in antibody directed enzyme prodrug therapy. In this methodology, an anti-tumor antibody is conjugated to an appropriate enzyme (e.g., carboxypeptidase G2) and allowed to localize to a tumor, while clearing from normal tissues. A non-toxic prodrug is then delivered, and is activated to a toxic drug specifically by enzyme at the tumor site. (See e.g. Bagshawe 1987, 1989, 1993; Bagshawe et al. 1988).

An enzyme that hydrolyzes an oxygen-carbonyl-nitrogen moiety may be used to convert the less readily converted carbamates of the invention (e.g. PG671, PG672, PG688). Antibody-conjugated enzymes capable of hydrolyzing a carbamate ester bond are known; see e.g. Wentworth et al. 1996. Accordingly, the above carbamates of triptolide may be useful as prodrugs that are significantly less toxic and would be liberated at a tumor site in the presence of antibody-conjugated enzymes.

VII. Therapeutic Compositions

Formulations containing the triptolide analogs of formula I may take the form of solid, semi-solid, lyophilized powder, or liquid dosage forms, such as tablets, capsules, powders, sustained-release formulations, solutions, suspensions, emulsions, ointments, lotions, or aerosols, preferably in unit dosage forms suitable for simple administration of precise dosages. The compositions typically include a conventional pharmaceutical carrier or excipient and may additionally include other medicinal agents, carriers, or adjuvants. Preferably, the composition will be about 0.5% to 75% by weight of a compound or compounds of formula I, with the remainder consisting of suitable pharmaceutical excipients. For oral administration, such excipients include pharmaceutical grades of mannitol, lactose, starch, magnesium stearate, sodium saccharine, talcum, cellulose, glucose, gelatin, sucrose, magnesium carbonate, and the like. If desired, the composition may also contain minor amounts of non-toxic auxiliary substances such as wetting agents, emulsifying agents, or buffers.

The composition may be administered to a subject orally, transdermally or parenterally, e.g., by intravenous, subcutaneous, intraperitoneal, or intramuscular injection. For use in oral liquid preparation, the composition may be prepared as a solution, suspension, emulsion, or syrup, being supplied either in liquid form or a dried form suitable for hydration in water or normal saline. For parenteral administration, an injectable composition for parenteral administration will typically contain the triptolide analog in a suitable intravenous solution, such as sterile physiological salt solution.

Liquid compositions can be prepared by dissolving or dispersing the triptolide analog (about 0.5% to about 20%) and optional pharmaceutical adjuvants in a carrier, such as, for example, aqueous saline, aqueous dextrose, glycerol, or ethanol, to form a solution or suspension. The high water solubility of the compounds of formula I make them particularly advantageous for administering in aqueous solution, e.g. by intraperitoneal injection. Although aqueous solutions are preferred, compositions in accordance with formula I may also be formulated as a suspension in a lipid (e.g., a triglyceride, a phospholipid, or a polyethoxylated castor oil such as "CREMOPHOR EL™"), in a liposomal suspension, or in an aqueous emulsion.

The compound may also be administered by inhalation, in the form of aerosol particles, either solid or liquid, preferably of respirable size. Such particles are sufficiently small to pass through the mouth and larynx upon inhalation and into the bronchi and alveoli of the lungs. In general, particles ranging from about 1 to 10 microns in size, and preferably less than about 5 microns in size, are respirable. Liquid compositions for inhalation comprise the active agent dispersed in an aqueous carrier, such as sterile pyrogen free saline solution or sterile pyrogen free water. If desired, the composition may be mixed with a propellant to assist in spraying the composition and forming an aerosol.

Methods for preparing such dosage forms are known or will be apparent to those skilled in the art; for example, see *Remington's Pharmaceutical Sciences* (19th Ed., Williams & Wilkins, 1995). The composition to be administered will contain a quantity of the selected compound in a pharmaceutically effective amount for effecting immunosuppression in a subject.

EXAMPLES

The following examples illustrate but are not intended in any way to limit the invention.

Example 1

Preparation of a Triptolide Carbamate by Reaction with an Isocyanate (General Procedure A)

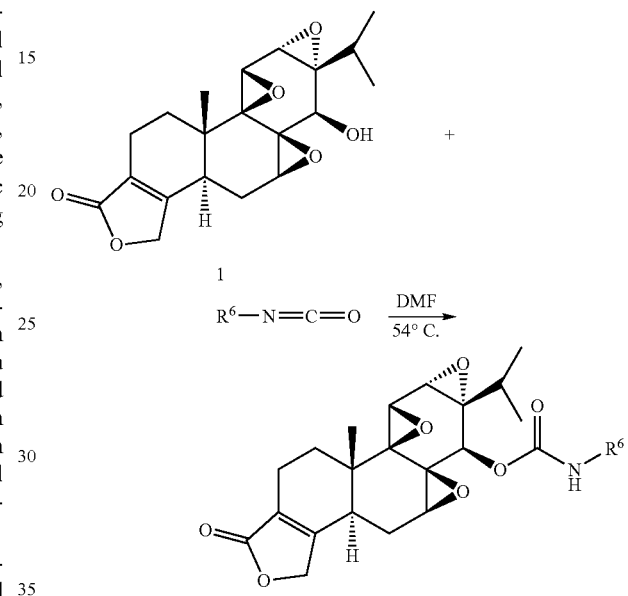

A mixture of triptolide, 1 (0.20 mmol, 1.0 eq) and an isocyanate (3.0 mmol, 15.0 eq) in N,N-dimethylformamide (DMF, 7.0 ml) is sealed and heated in 54° C. oil bath with stirring. The reaction is monitored with TLC. After the starting material is completely consumed, the reaction mixture is concentrated under vacuum, and the crude product is purified with preparative TLC.

Example 2

Preparation of a Triptolide Carbamate by Reaction with Phosgene and an Amine (General Procedure B)

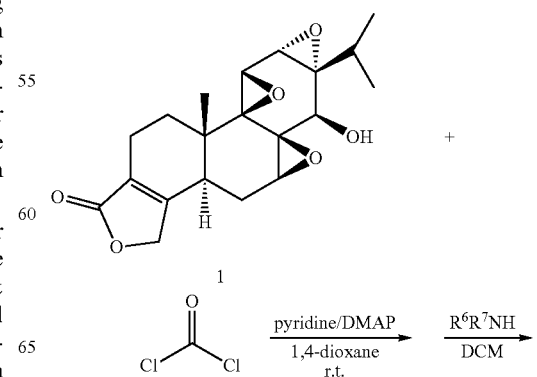

-continued

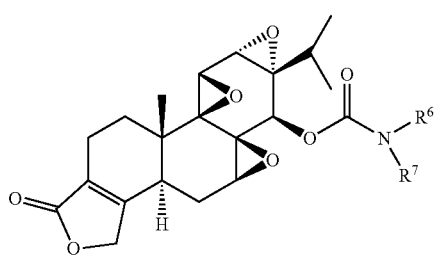

To a solution of triptolide, 1 (0.325 mmol, 1.0 eq) and 4-dimethylaminopyridine (DMAP, 0.0377 mmol, 0.12 eq) in 1,4-dioxane (15 ml) is added with stirring pyridine (1.0 ml) and phosgene (20% in toluene, 1.19 ml, 2.25 mmol, 6.92 eq) at room temperature under nitrogen. After 1 hour of stirring at room temperature, the reaction mixture is concentrated under vacuum. To the residue is added dichloromethane (DCM, 15.0 ml) and then the amine ($R^6R^7NH$, 1.0 ml). After 10 minutes of stirring at room temperature, the reaction mixture is concentrated under vacuum, and the crude product is purified with preparative TLC.

Example 3

Preparation of a Triptolide Carbonate by Reaction with a Chloroformate (General Procedure C)

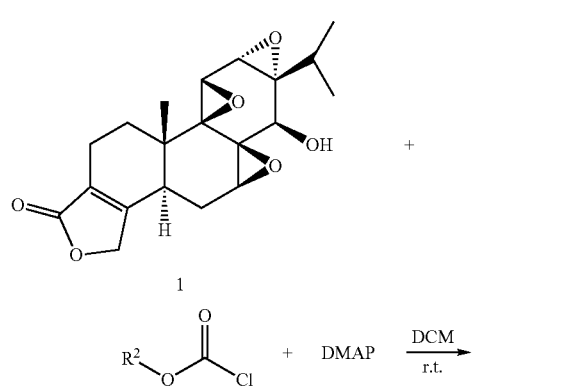

To a solution of triptolide, 1 (0.33 mmol, 1.0 eq) and 4-dimethylaminopyridine (DMAP, 3.92 mmol, 11.9 eq) in dichloromethane (DCM, 15 ml) is added with stirring a chloroformate (2.15 mmol, 6.5 eq) at room temperature under nitrogen. After 24 hours of stirring at room temperature, the reaction mixture is concentrated under vacuum, and the crude product is purified with preparative TLC.

Example 4

Preparation of a Triptolide Carbonate by Reaction with Phosgene and an Alcohol (General Procedure D)

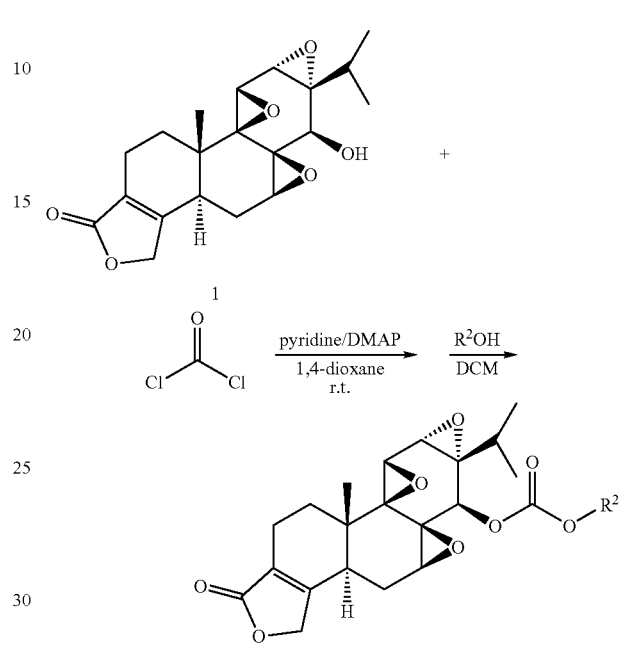

To a solution of triptolide, 1 (0.30 mmol, 1.0 eq) and 4-dimethylaminopyridine (DMAP, 3.60 mmol, 12.0 eq) in 1,4-dioxane (15 ml) is added with stirring phosgene (20% in toluene, 0.79 ml, 1.50 mmol, 5.0 eq) at room temperature under nitrogen. After 1 hour of stirring at room temperature, the reaction mixture is concentrated under vacuum. To the residue is added dichloromethane (DCM, 15 ml) and then the alcohol ($R^2OH$, 1.0 ml). After stirring at room temperature overnight, the reaction mixture is concentrated under vacuum, and the crude product is purified with preparative TLC.

Example 5

Synthesis of Triptolide 14-Ethyl Carbamate (PG666)

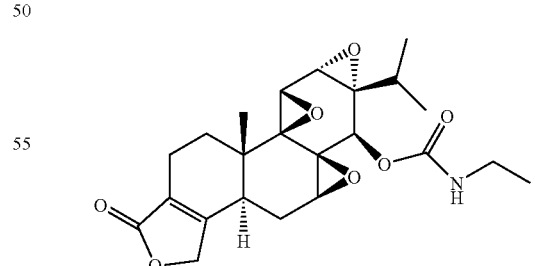

Using General Procedure A, the product was obtained in 98.5% yield from ethyl isocyanate and triptolide. Analytical TLC Rf=0.44 (ethyl acetate/hexanes/methanol 1:1:0.1). IR (KBr): 3369.6, 2975.6, 2937.6, 2878.0, 1753.0, 1719.0, 1686.1, 1676.5, 1524.0, 1517.7, 1509.0, 1458.7, 1448.8, 1245.8, 1142.5, 1076.3, 1030.8, 988.1, 944.4, 866.9, 722.6, 560.5 cm$^{-1}$. H$^1$ NMR (300 MHz, CDCl$_3$): δ=4.94 (1H, s, 14-CH), 4.68 (2H, s, 19-CH$_2$), 3.83 (1H, d, 11-CH), 3.51 (1H, d, 12-CH), 3.48 (1H, d, 7-CH), 3.26 {2H, m, 22-CH$_2$ (—NCH$_2$CH$_3$)}, 2.70 (1H, m, 5-CH), 2.32 (1H, m, 2-CHb), 2.13 (2H, m, 6-CHb and 2-CHa), 1.93 (2H, m, 15-CH and 6-CHa), 1.57 (1H, dd, 1-CHb), 1.22 (1H, m, 1-CHa), 1.16 {3H, t, 23-CH$_3$ (—NCH$_2$CH$_3$)}, 1.07 (3H, s, 20-CH$_3$), 0.99 (3H, d, 17-CH$_3$), 0.86 (3H, d, 16-CH$_3$) ppm. HRMS (FAB) m/z calcd for C$_{23}$H$_{30}$NO$_7^+$ (MH$^+$) 432.2022, found 432.2016.

Example 6

Synthesis of Triptolide 14-Phenyl Carbamate (PG671)

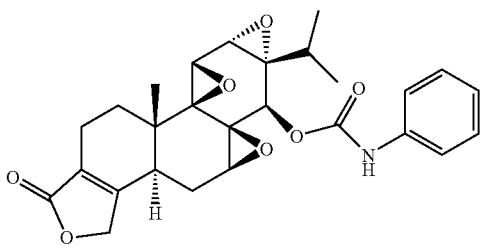

Using General Procedure A, the product was obtained in 87.0% yield from phenyl isocyanate and triptolide. Analytical TLC Rf=0.51 (ethyl acetate/hexanes/methanol 1:1:0.1). IR (KBr): 3315.3, 2970.4, 2939.5, 2878.3, 1751.9, 1676.6, 1600.8, 1543.0, 1534.7, 1443.6, 1314.6, 1215.3, 1063.3, 1028.5, 761.0, 693.1 cm$^{-1}$. H$^1$NMR (300 MHz, CDCl$_3$): δ=7.43 (2H, d, Ar—H), 7.30 (2H, dd, Ar—H), 7.07 (1H, t, Ar—H), 5.04 (1H, s, 14-CH), 4.82 (2H, s, 19-CH$_2$), 3.88 (1H, d, 11-CH), 3.57 (1H, d, 12-CH), 3.52 (1H, d, 7-CH), 2.67 (1H, m, 5-CH), 2.33 (1H, d, 2-CHb), 2.17 (2H, m, 6-CHb and 2-CHa), 1.96 (2H, m, 15-CH and 6-CHa), 1.58 (1H, dd, 1-CHb), 1.25 (1H, m, 1-CHa), 1.08 (3H, s, 20-CH$_3$), 1.02 (3H, d, 17-CH$_3$), 0.88 (3H, d, 16-CH$_3$) ppm.

Example 7

Synthesis of Triptolide 14-Dimethylaminoethyl Carbamate (PG688)

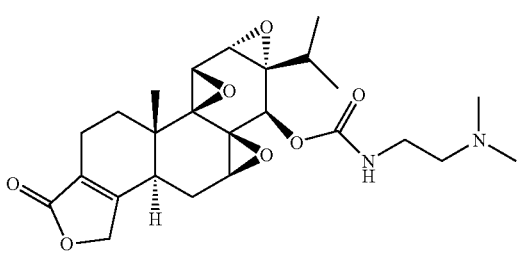

Using General Procedure B, the product was obtained in 79.9% yield from triptolide, phosgene and N,N-dimethylethylenediamine. Analytical TLC Rf=0.45 (ethyl acetate/hexanes/methanol/triethylamine 1.2:0.8:0.2:0.1). IR (KBr): 3380.1, 2969.6, 2827.2, 2780.3, 1753.4, 1720.3, 1675.8, 1560.7, 1542.0, 1523.8, 1459.4, 1448.6, 1388.3, 1348.3, 1254.3, 1132.9, 1069.9, 1023.7, 888.2, 773.7, 561.0, 522.3 cm$^{-1}$. H$^1$ NMR (300 MHz, CDCl$_3$): δ=5.57 (1H, t, CONH—), 4.94 (1H, s, 14-CH), 4.68 (2H, s, 19-CH$_2$), 3.83 (1H, d, 11-CH), 3.52 (1H, d, 12-CH), 3.48 (1H, d, 7-CH), 3.31 {2H, m, 22-CH$_2$ (CONHCH$_2$CH$_2$)}, 2.69 (1H, m, 5-CH), 2.48 {2H, dd, 23-CH$_2$ (CONHCH$_2$CH$_2$—)}, 2.34 (1H, m, 2-CHb), 2.27 {6H, s, —N(CH$_3$)$_2$}, 2.23-2.13 (2H, m, 2-CHa and 6-CHb), 2.03-1.84 (2H, m, 15-CH and 6-CHa), 1.58 (1H, dd, 1-CHb), 1.21 (1H, m, 1-CHa), 1.07 (3H, s, 20-CH$_3$), 0.99 (3H, d, 17-CH$_3$), 0.85 (3H, d, 16-CH$_3$) ppm.

Example 8

Synthesis of Triptolide 14-Ethyl Carbonate (PG674)

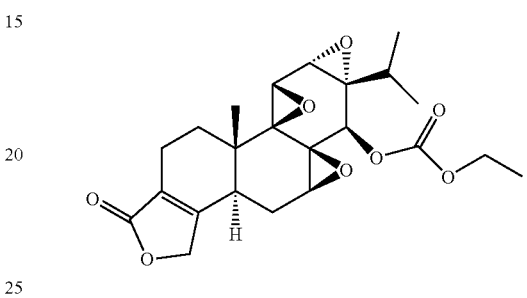

Using General Procedure C, the product was obtained in 89.6% yield from ethyl chloroformate and triptolide. Analytical TLC Rf=0.58 (ethyl acetate/hexanes/methanol 1:1:0.1). IR (KBr): 2972.3, 2938.3, 2879.4, 1474.3, 1677.0, 1448.0, 1372.0, 1253.5, 1170.1, 1092.8, 1068.5, 1004.4, 962.3, 912.3, 864.6, 786.0, 560.1 cm$^{-1}$. H$^1$ NMR (300 MHz, CDCl$_3$): δ=4.83 (1H, s, 14-CH), 4.68 (2H, q, 19-CH$_2$), 4.25 {2H, qd, 22-CH$_2$ (—OCH$_2$CH$_3$)}, 3.82 (1H, d, 11-CH), 3.55 (1H, dd, 12-CH), 3.49 (1H, d, 7-CH), 2.70 (1H, m, 5-CH), 2.32 (1H, m, 2-CHb), 2.19 (2H, m, 6-CHb and 2-CHa), 1.96 (2H, m, 15-CH and 6-CHa), 1.61 (1H, m, 1-CHb), 1.37 {3H, t, 23-CH$_3$ (—OCH$_2$CH$_3$)}, 1.21 (1H, m, 1-CHa), 1.07 (3H, s, 20-CH$_3$), 0.99 (3H, d, 17-CH$_3$), 0.86 (3H, d, 16-CH$_3$) ppm.

Example 9

Synthesis of Triptolide 14-Phenyl Carbonate (PG676)

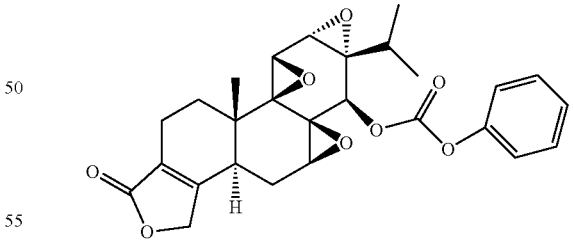

Using General Procedure C, the product was obtained in 78.8% yield from phenyl chloroformate and triptolide. Analytical TLC Rf=0.53 (ethyl acetate/hexanes/methanol 1:1:0.1). IR (KBr): 2969.7, 2937.6, 1752.1, 1676.5, 1442.6, 1265.6, 1210.6, 1021.5, 961.8, 910.7, 774.3, 560.6 cm$^{-1}$. H$^1$ NMR (300 MHz, CDCl$_3$): δ=7.42-7.20 (5H, m, Ar—H), 4.83 (1H, s, 14-CH), 4.68 (2H, q, 19-CH$_2$), 3.83 (1H, d, 11-CH), 3.55 (1H, dd, 12-CH), 3.49 (1H, d, 7-CH), 2.68 (1H, m, 5-CH), 2.32 (1H, m, 2-CHb), 2.19 (2H, m, 6-CHb and 2-CHa), 1.96 (2H, m, 15-CH and 6-CHa), 1.49 (1H, m, 1-CHb), 1.24 (1H, m, 1-CHa), 1.07 (3H, s, 20-CH₃), 0.99 (3H, d, 17-CH₃), 0.86 (3H, d, 16-CH₃) ppm.

Example 10

Synthesis of Triptolide 14-Ethoxyethyl Carbonate (PG679)

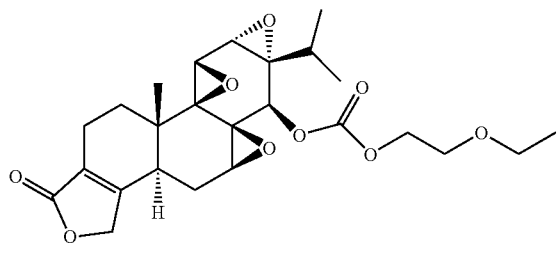

Using General Procedure D, the product was obtained in 90.2% yield from triptolide, phosgene and ethoxyethanol. Analytical TLC Rf=0.49 (ethyl acetate/hexanes/methanol 1:1:0.1). IR (KBr): 2974.0, 2935.3, 2876.5, 1750.8, 1676.4, 1458.6, 1448.6, 1388.7, 1375.8, 1122.3, 1023.0, 962.3, 910.8, 866.1, 784.1, 751.6, 559.7 cm⁻¹. H¹NMR (300 MHz, CDCl₃): δ=4.83 (1H, s, 14-CH), 4.80 (2H, q, 19-CH₂), 4.40 {1H, m, 22-CHb (OCOOCHaHbCH₂)}, 4.27 {1H, m, 22-CHa (OCOOCHaHbCH₂—)}, 3.82 (1H, d, 11-CH), 3.68 {2H, m, 23-CH₂ (OCOOCH₂CH₂—)}, 3.54 {3H, m, 12-CH and 24-CH₂ (—OCH₂CH₃)}, 3.48 (1H, d, 7-CH), 2.68 (1H, m, 5-CH), 2.31 (1H, m, 2-CHb), 2.18 (2H, m, 2-CHa and 6-CHb), 1.96 (2H, m, 15-CH and 6-CHa), 1.58 (1H, dd, 1-CHb), 1.21 {4H, 1-CHa and 25-CH₃ (OCH₂CH₃)}, 1.07 (3H, s, 20-CH₃), 0.99 (3H, d, 17-CH₃), 0.85 (3H, d, 16-CH₃) ppm.

Example 11

Synthesis of Triptolide 14-(R)-α-Methyl-tert-butoxycarbonylmethyl Carbonate (PG681)

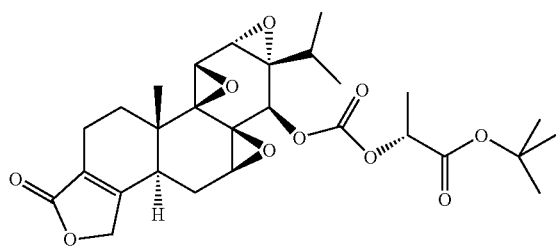

Using General Procedure D, the product was obtained in 76.2% yield from triptolide, phosgene and tert-butyl (R)-(+)-lactate. Analytical TLC Rf=0.62 (ethyl acetate/hexanes/methanol 1:1:0.1). IR (KBr): 2979.5, 2938.3, 2880.6, 1754.6, 1676.9, 1474.0, 1458.1, 1370.1, 1351.6, 1318.0, 1264.2, 1165.7, 1136.2, 1116.3, 1074.7, 1031.2, 962.5, 912.6, 866.8, 843.6, 786.2, 560.6 cm⁻¹. H¹ NMR (300 MHz, CDCl₃): δ=4.85 {1H, q, 22-CH [OCOOCH(CH₃)CO]}, 4.83 (1H, s, 14-CH), 4.68 (2H, q, 19-CH₂), 3.83 (1H, d, 11-CH), 3.56 (1H, dd, 12-CH), 3.48 (1H, d, 7-CH), 2.65 (1H, m, 5-CH), 2.31 (1H, m, 2-CHb), 2.23-2.04 (3H, m, 6-CHb, 2-CHa and 15-CH), 1.93 (1H, dd, 6-CHa), 1.59 (1H, dd, 1-CHb), 1.52 {3H, d, 28-CH₃ [OCOOCH(CHF₃)CO]}, 1.45 {9H, s, OC(CH₃)₃}, 1.19 (1H, m, 1-CHa), 1.08 (3H, s, 20-CH₃), 1.01 (3H, d, 17-CH₃), 0.87 (3H, d, 16-CH₃) ppm.

Example 12

Synthesis of Triptolide 14-Methoxycarbonylmethyl Carbonate (PG680)

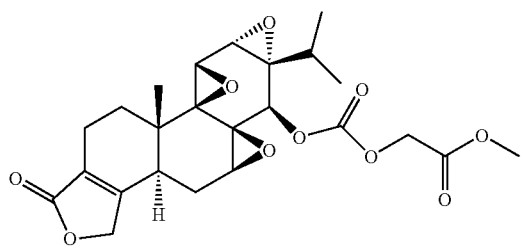

Using General Procedure D, the product was obtained in 82.4% yield from triptolide, phosgene and methyl glycolate. Analytical TLC Rf=0.45 (ethyl acetate:hexanes:methanol 1:1:0.1). IR (KBr): 2967.9, 2882.3, 1751.9, 1676.6, 1439.5, 1383.0, 1283.9, 1245.5, 1213.3, 1022.0, 1005.0, 962.1, 910.7, 783.1, 560.6, 547.9, 530.6, 521.5, 478.7 cm⁻¹. H¹ NMR (300 MHz, CDCl₃): δ=4.84 (1H, s, 14-CH), 4.80 {1H, d, 22-CHb (OCOOCHaHbCO)}, 4.68 (2H, q, 19-CH₂), 4.57 {1H, d, 22-CHa (OCOOCHaHbCO)}, 3.83 (1H, d, 11-CH), 3.79 {3H, s, 24-CH₃ (—OCH₃)}, 3.56 (1H, dd, 12-CH), 3.49 (1H, d, 7-CH), 2.70 (1H, m, 5-CH), 2.32 (1H, m, 2-CHb), 2.23-2.14 (2H, m, 2-CHa and 6-CHb), 2.07-1.89 (2H, m, 15-CH and 6-CHa), 1.59 (1H, m, 1-CHb), 1.23 (1H, m, 1-CHa), 1.08 (3H, s, 20-CH₃), 1.02 (3H, d, 17-CH₃), 0.89 (3H, d, 16-CH₃) ppm.

Example 13

Synthesis of Triptolide 14-Dimethylaminoethyl Carbonate (PG682)

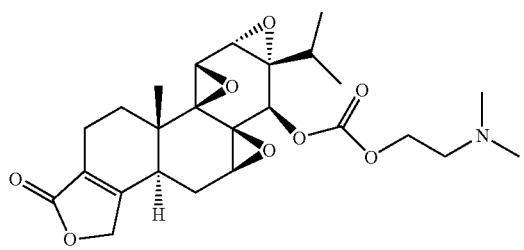

Using General Procedure D, the product was obtained in 71.2% yield from triptolide, phosgene and dimethylaminoethanol. Analytical TLC Rf=0.24 (ethyl acetate:hexanes: methanol:triethylamine 1:1:0.1:0.02). IR (KBr): 2969.4, 2824.8, 2772.3, 1751.1, 1676.2, 1671.3, 1655.0, 1473.9, 1466.0, 1375.1, 1254.9, 1020.4, 992.6, 962.7, 910.6, 778.9, 557.4, 517.1, 472.4, 440.7 cm⁻¹. H¹NMR (300 MHz, CDCl₃): δ=4.83 (1H, s, 14-CH), 4.68 (2H, s, 19-CH₂), 4.34 {2H, m, 22-CH₂ (OCOOCH₂CH₂N)}, 3.82 (1H, d, 11-CH), 3.55 (1H, d, 12-CH), 3.49 (1H, d, 7-CH), 2.75-2.62 {3H, m, 23-CH₂ (OCOOCH₂CH₂N) and 5-CH}, 2.37 (6H, s, —N(CH$_3$)$_2$}, 2.31 (1H, m, 2-CHb), 2.23-2.15 (2H, m, 2-CHa and 6-CHb), 2.04-1.89 (2H, m, 15-CH and 6-CHa), 1.58 (1H, dd, 1-CHb), 1.21 (1H, m, 1-CHa), 1.06 (3H, s, 20-CH$_3$), 0.99 (3H, d, 17-CH$_3$), 0.85 (3H, d, 16-CH$_3$) ppm. HRMS (FAB) m/z calcd for C$_{25}$H$_{34}$NO$_8$$^+$ (MH$^+$) 476.2284, found 476.2289.

Example 14

Synthesis of p-Toluenesulfonate Salt of Triptolide 14-Dimethylaminoethyl Carbonate (PG682 PTSA)

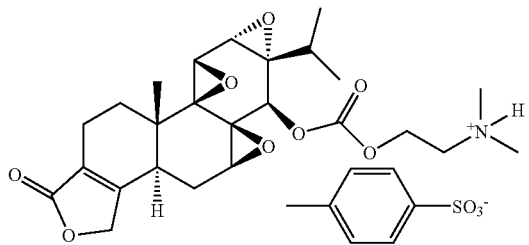

With stirring, to a solution of p-toluenesulfonic acid (19.0 mg, 0.10 mmol) in H$_2$O (8.0 ml) was slowly added triptolide 14-dimethylaminoethyl carbonate (PG682) (47.6 mg, 0.10 mmol). After the addition, the solution was stirred for another 30 minutes and then lyophilized to yield 60.5 mg (93.4%) of white powder. IR (KBr): 3445.0, 3035.8, 2972.1, 2730.1, 1750.9, 1676.1, 1671.9, 1664.8, 1655.4, 1638.1, 1459.3, 1256.2, 1169.3, 1121.7, 1033.3, 1010.3, 961.0, 910.7, 817.9, 683.0, 570.4, 479.0 cm$^{-1}$. H$^1$ NMR (300 MHz, DMSO-d$_6$): δ=7.47 (2H, d, Ar—H), 7.10 (2H, d, Ar—H), 4.82 (2H, q, 19-CH$_2$), 4.80 (1H, s, 14-CH), 4.46 {2H, m, 22-CH$_2$ (OCOO CH$_2$CH$_2$N)}, 3.97 (1H, d, 11-CH), 3.73 (1H, d, 12-CH), 3.67 (1H, d, 7-CH), 3.44 {2H, m, 23-CH$_2$ (OCOOCH$_2$CH$_2$N)}, 2.83 (3H, s, Ar—CH$_3$), 2.63 (1H, m, 5-CH), 2.28 {6H, s, —N(CH$_3$)$_2$}, 2.22 (1H, m, 6-CHb), 2.15 (1H, m, 2-CHb), 2.09 (1H, m, 2-CHa), 1.98 (1H, m, 1-CHb), 1.90 (1H, m, 15-CH), 1.81 (1H, dd, 6-CHa), 1.30 (1H, m, 1-CHa), 0.91 (3H, s, 20-CH$_3$), 0.90 (3H, d, 17-CH$_3$), 0.78 (3H, d, 16-CH$_3$) ppm.

Example 15

Synthesis of Triptolide 14-Hydroxycarbonylmethyl Carbonate (PG687)

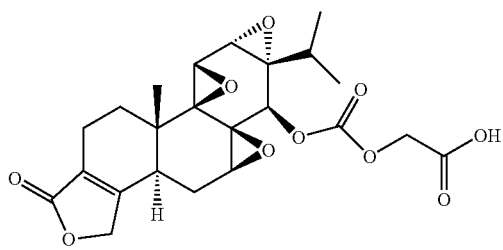

Using General Procedure D, the product was obtained in 47.8% yield from triptolide, phosgene and glycolic acid. Analytical TLC Rf=0.32 (ethyl acetate:hexanes:methanol acetic acid 1:1:0.1:0.1). IR (KBr): 3416.0, 2975.4, 1752.6, 1701.4, 1685.8, 1638.3, 1559.5, 1415.9, 1257.7, 1021.3, 810.3, 643.0, 528.0 cm$^{-1}$. H$^1$NMR (300 MHz, MeOH-d$_4$): δ=4.85 (1H, s, 14-H), 4.82 {2H, q, 22-CH$_2$ (OCOOCH$_2$CO)}, 4.46 (2H, q, 19-CH$_2$), 3.95 (1H, d, 11-CH), 3.65 (1H, d, 12-CH), 3.50 (1H, d, 7-CH), 2.78 (1H, m, 5-CH), 2.34-2.20 (2H, m, 6-CHb and 2-CHb), 2.08 (1H, m, 15-CH), 1.99-1.62 (2H, m, 2-CHa and 6-CHa), 1.50 (1H, dd, 1-CHb), 1.34 (1H, td, 1-CHa), 1.04 (3H, s, 20-CH$_3$), 0.98 (3H, d, 17-CH$_3$), 0.85 (3H, d, 16-CH$_3$) ppm. HRMS (FAB) m/z calcd for C$_{23}$H$_{26}$NaO$_{10}$$^+$ (MNa$^+$) 485.1424, found 485.1434.

Example 16

Synthesis of Sodium Salt of Triptolide 14-Hydroxycarbonylmethyl Carbonate (PG687 Na)

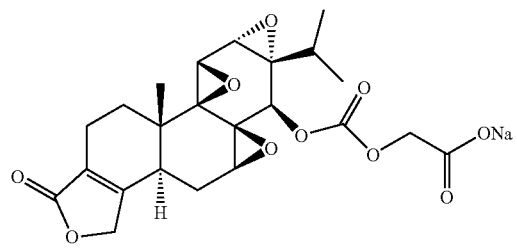

To a solution of NaHCO$_3$ (5.18 mg, 0.0616 mmol) in H$_2$O (3.9 ml) was slowly added triptolide 14-hydroxycarbonylmethyl carbonate (PG687) (28.5 mg, 0.0616 mmol) with stirring. After the addition, the solution was stirred for another 30 minutes and then lyophilized to yield 29.7 mg (99.3%) of white powder. IR (KBr): 2961.4, 2877.2, 1638.1, 1560.8, 1551.2, 1412.0, 1261.8, 1021.0, 803.4, 641.0, 530.6, 523.5 cm$^{-1}$. H$^1$ NMR (300 MHz, DMSO-d$_6$): δ=4.82 {2H, q, 22-CH$_2$ (OCOOCH$_2$CO)}, 4.70 (1H, s, 14-CH), 4.16 (1H, d, 19-CHb), 3.98 (1H, d, 19-CHa), 3.94 (1H, d, 11-CH), 3.69 (1H, d, 12-CH), 3.57 (1H, d, 7-CH), 2.58 (1H, m, 5-CH), 2.22 (1H, m, 6-CHb), 2.11 (1H, m, 2-CHb), 1.97 (2H, m, 2-CHa and 15-CH), 1.81 (1H, m, 6-CHa), 1.49 (1H, m, 1-CHb), 1.30 (1H, m, 1-CHa), 0.92 (3H, s, 20-CH$_3$), 0.90 (3H, d, 17-CH$_3$), 0.75 (3H, d, 16-CH$_3$) ppm.

Example 17

Synthesis of Tris(hydroxymethyl)aminomethane Salt of Triptolide 14-Hydroxycarbonyl-methyl Carbonate (PG687 tris)

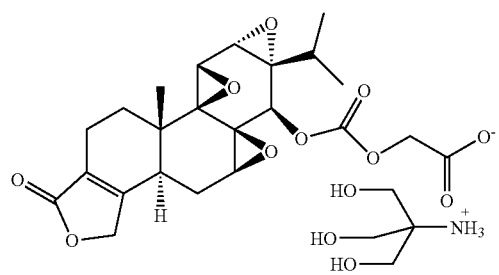

To a suspension of triptolide 14-hydroxycarbonylmethyl carbonate (PG687) (8.3 mg, 0.018 mmol) was added a solution of tris(hydroxymethyl)aminomethane (2.17 mg, 0.018 mmol) in H$_2$O (0.75 ml) with stirring. After the addition, the solution was stirred for another 30 minutes and then lyophilized. The powder was dissolved in $H_2O$ (2.0 ml) and filtered through a pad of cotton to remove the fine particles. The filtrate was then lyophilized to yield 10.1 mg (96.5%) of white powder. IR (KBr): 3364.5 (br), 2975.8, 1750.1, 1581.1, 1413.7, 1349.8, 1255.7, 1019.0, 968.5, 911.1, 648.9, 619.6, 561.2, 497.8 cm$^{-1}$. H$^1$NMR (300 MHz, DMSO-d$_6$): δ=4.82 {2H, q, 22-CH$_2$ (OCOOC$\underline{H}_2$CO)}, 4.70 (1H, s, 14-CH), 4.20 (1H, d, 19-CHb), 4.02 (1H, d, 19-CHa), 3.94 (1H, d, 11-CH), 3.69 (1H, d, 12-CH), 3.56 (1H, d, 7-CH), 3.20 (6H, s, (HO C$\underline{H}_2$)$_3$CNH$_2$}, 2.61 (1H, m, 5-CH), 2.22 (1H, m, 6-CHb), 2.11 (1H, m, 2-CHb), 1.96 (2H, m, 2-CHa and 15-CH), 1.81 (1H, m, 6-CHa), 1.30 (2H, m, 1-CH$_2$), 0.91 (3H, s, 20-CH$_3$), 0.90 (3H, d, 17-CH$_3$), 0.76 (3H, d, 16-CH$_3$) ppm.

Example 18

Synthesis of Triptolide 14-tert-Butyl Carbonate (PG695)

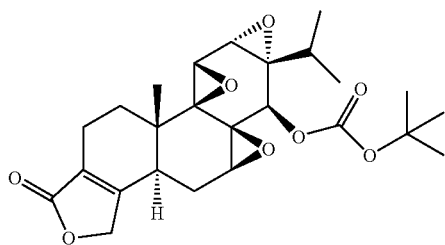

To a solution of triptolide (108.1 mg, 0.30 mmol, 1.0 eq) and 4-DMAP (367.0 mg, 3.0 mmol, 10.0 eq) in dichloromethane (15 ml) was added with stirring di-tert-butyl dicarbonate (393.0 mg 1.80 mmol, 6.0 eq) at room temperature under nitrogen. After 48 hours of stirring at room temperature, methyl alcohol (1.0 ml) was added. The reaction mixture was concentrated under vacuum and the crude product was purified with preparative TLC (ethyl acetate/hexanes/methanol 1:1:0.1) to give 131.3 mg (95.1%) of the desired product. Analytical TLC Rf=0.66 (ethyl acetate/hexanes/methanol 1:1:0.1). IR (KBr): 2976.7, 2938.5, 1738.2, 1676.7, 1444.6, 1394.6, 1370.5, 1335.2, 1278.4, 1254.5, 1160.1, 1118.2, 1091.8, 1020.2, 991.6, 962.9, 912.0, 854.4, 786.4, 751.5, 607.2, 558.2, 529.3, 478.2 cm$^{-1}$. H$^1$ NMR (300 MHz, CDCl$_3$): δ=4.80 (1H, s, 14-CH), 4.68 (2H, q, 19-CH$_2$), 3.81 (1H, d, 11-CH), 3.53 (1H, d, 12-CH), 3.46 (1H, d, 7-CH), 2.69 (1H, m, 5-CH), 2.35 (1H, m, 2-CHb), 2.18 (2H, m, 6-CHb and 2-CHa), 1.96 (2H, m, 15-CH and 6-CHa), 1.61 (1H, m, 1-CHb), 1.51 {9H, s, —OC(CH$_3$)$_3$}, 1.24 (1H, m, 1-CHa), 1.08 (3H, s, 20-CH$_3$), 0.99 (3H, d, 17-CH$_3$), 0.86 (3H, d, 16-CH$_3$) ppm.

Example 19

Apoptosis Assays

A. Incubation of compounds with human serum. Pooled human serum was stored in aliquots at −80° C. Test compounds were added at 20 mM to thawed human serum in 1.5 ml microfuge tubes and incubated at 37° C. in a water bath for varying periods of time. The test samples were placed on ice until dilution for the bioassay. Controls consisted of the compounds incubated in complete tissue culture medium (RPMI 1640 medium plus 5% heat-inactivated fetal calf serum, 1% HEPES, 1% pen/strep, 1% glutamine) rather than human serum.

B. Apoptosis assay of compounds incubated with human serum. Test samples were diluted to 1 mM in complete tissue culture medium. Aliquots were placed in microculture plates and serial dilutions were prepared so that the final concentration would encompass the range of 1 to 10,000 nM with half-log increments. Cells from an exponentially expanding culture of the Jurkat human T lymphocyte cell line (#TIB-152 obtained from American Type Culture Collection, Manassas, Va.) were harvested, washed once by centrifugation and dilution in complete tissue culture medium, and diluted to a concentration of 1×10$^6$ cells/ml. A volume of 100 μl of Jurkat cells (1×10$^5$ cells) was added to wells containing 100 μl of the diluted compounds, and the plates were incubated at 37° C. in a 5% CO$_2$ incubator. After 24 hours, the plates were centrifuged to pellet the cells, and the cells were washed twice with 2% heat-inactivated fetal calf serum in PBS. To each well, 500 ul of binding buffer was added according to the Annexin V assay procedure (BioVision, Inc., Mountain View, Calif.). Next, 5 μl of the fluorescein isothiocyanate (FITC) conjugate of Annexin V (BioVision, Inc.) was added to each well, followed by 5 minutes of incubation in the dark. In some assays, propidium iodide (BioVision, Inc.) was added at this stage to check for necrotic cells. The contents of the wells were individually transferred into test tubes, and apoptosis was analyzed using a FACSCalibur flow cytometer (BD Immunocytometry Systems, San Jose, Calif.). Cells positive for Annexin V binding were considered to be apoptotic, and the data were calculated as percent apoptotic cells.

C. Comparison of bioactivities after incubation of compounds in human serum. The data were plotted as the concentration of compound incubated in serum versus percent apoptotic cells. The concentration of compound inducing 50% apoptosis (ED$_{50}$) was calculated from these dose response curves. The percent conversion of the test compounds to bioactive compounds (assumed to be triptolide) was calculated in reference to the result with triptolide incubated in parallel in human plasma in the same experiment, as the percent of the ED$_{50}$ of the compound compared to that for triptolide, which was taken as 100%. This percentage conversion was used to compare the bioactivity of various compounds after incubation in human serum.

Example 20

Immunosuppression Assays

A. IL-2 production assay for activity of compounds incubated with human serum. Test samples were diluted to 1 mM in complete tissue culture medium. Aliquots were placed in microculture plates that had been coated with anti-CD3 antibody (used to stimulate the production of IL-2 by Jurkat cells) and serial dilutions were prepared so that the final concentration would encompass the range of 0.001 to 10,000 nM in log increments. Cells from an exponentially expanding culture of the Jurkat human T lymphocyte cell line (#TIB-152 obtained from American Type Culture Collection, Manassas, Va.) were harvested, washed once by centrifugation and dilution in complete tissue culture medium, and diluted to a concentration of 2×10$^6$ cells/ml. A volume of 50 μl of Jurkat cells (1×10$^5$ cells) was added to wells containing 100 μl of the diluted compounds, 50 μl of PMA (10 ng/ml) was added to each well, and the plates were incubated at 37° C. in a 5% CO$_2$ incubator. After 24 hours, the plates were centrifuged to pellet the cells, 150 μl of supernatant was removed from each well, and the samples were stored at −20° C. The stored supernatants were analyzed for human IL-2 concentration using the Luminex 100 (Luminex Corporation, Austin, Tex.), Luminex microspheres coupled with anti-IL-2 capture antibody, and fluorochrome-coupled anti-IL-2 detection antibody. The data were expressed as ng/ml of IL-2.

B. Comparison of bioactivities after incubation of compounds in human serum. The data were plotted as the concentration of compound incubated in serum versus IL-2 concentration. The concentration of compound inducing a 50% decrease in the IL-2 concentration ($IC_{50}$) was calculated from these dose response curves. The percent conversion of the test compounds to bioactive compounds (assumed to be triptolide) was calculated in reference to the result with triptolide incubated in parallel in human plasma in the same experiment, as the percent of the $IC_{50}$ of the compound compared to that for triptolide, which was taken as 100%. This percentage conversion was used to compare the bioactivity of various compounds after incubation in human serum.

It is claimed:

1. A compound having the structure I:

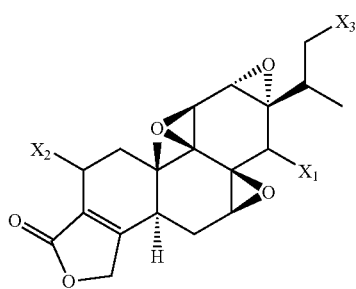

where
$X^1$ is OH or $OR^1$, and $X^2$ and $X^3$ are independently OH, $OR^1$ or H, with the proviso that at least one of $X^1$, $X^2$ and $X^3$ is $OR^1$, and at least one of $X^2$ and $X^3$ is H; and
$OR^1$ is O—(C=O)-Z, where Z is selected from the group consisting of: —$OR^2$, —O—Y—(C=O)—$OR^3$, —O—Y—$NR^4R^5$, —$NR^4R^5$, —$NR^3$—Y—(C=O)—$OR^3$, and —$NR^3$—Y—$N^4N^5$;
wherein
Y is a divalent alkyl, alkenyl or alkynyl group having up to six carbon atoms;
$R^2$ is selected from alkyl, alkenyl, alkynyl, cycloalkyl, cycloalkenyl, aryl, aralkyl, hydroxyalkyl, alkoxyalkyl, aryloxyalkyl, and acyloxyalkyl;
each $R^3$ is independently selected from hydrogen and $R^2$; and
$R^4$ and $R^5$ are independently selected from hydrogen, alkyl, alkenyl, alkynyl, cycloalkyl, cycloalkenyl, aryl, aralkyl, hydroxyalkyl, alkoxyalkyl, aryloxyalkyl, and acyloxyalkyl, or $R^4$ and $R^5$ taken together form a 5- to 7-member heterocyclic ring whose ring atoms are selected from the group consisting of carbon, nitrogen, oxygen and sulfur, wherein said ring atoms include at most 3 heteroatoms.

2. The compound of claim 1, wherein $X^2$=$X^3$=H.

3. The compound of claim 2, wherein Y is —$CH_2$— or —$CH_2CH_2$—.

4. The compound of claim 2, wherein $OR^1$ is selected from the group consisting of O—(C=O)—$OR^2$, O—(C=O)—O—Y—(C=O)—$OR^3$, and O—(C=O)—O—Y—$NR^4R^5$.

5. The compound of claim 1, wherein each of the groups defined as $R^2$, $R^3$, $R^4$, and $R^5$, when selected from alkyl, alkenyl, and alkynyl, have up to six carbon atoms; when defined as cycloalkyl, have 3 to 7 carbon atoms; when defined as cycloalkenyl, have 5 to 7 carbon atoms; and when selected from aralkyl, hydroxyalkyl, alkoxyalkyl, aryloxyalkyl, and acyloxyalkyl, have alkyl components with up to six carbon atoms.

6. The compound of claim 5, wherein each of $R^2$, $R^3$, $R^4$, and $R^5$ is independently selected from the group consisting of alkyl having up to six carbon atoms, aryl, aralkyl, and alkoxyalkyl.

7. The compound of claim 2, wherein $OR^1$ is -selected from the group consisting of O—(C=O)—$NR^4R^5$, O—(C=O)—$NR^3$—Y—(C=O)—$OR^3$, and O—(C=O)—$NR^3$—Y—$NR^4N^5$.

8. The compound of claim 7, wherein each of $R^3$, $R^4$, and $R^5$ is independently selected from the group consisting of alkyl having up to six carbon atoms, aryl, aralkyl, and alkoxyalkyl.

9. The compound of claim 1, where $X^1$ is $OR^1$, and $X^2$ and $X^3$ are H; and
$OR^1$ is O—(C=O)-Z, where Z is —$OR^2$; and $R^2$ is alkyl having up to six carbon atoms.

10. The compound of claim 9, wherein $X^1$ is —O—(C=O)—O—$CH_2CH_3$.

11. The compound of claim 9, wherein $X^1$ is —O—(C=O)—O—$C(CH_3)_3$.

12. A compound selected from the group consisting of: PG666 (Triptolide 14-ethyl carbamate), PG671 (Triptolide 14-phenyl carbamate), PG672 (Triptolide N-methylpiperazinecarbonyl carbamate), PG674 (Triptolide 14-ethyl carbonate), PG676 (Triptolide 14-phenyl carbonate), PG679 (Triptolide 14-ethoxyethyl carbonate ), PG680 (Triptolide 14-methoxycarbonylmethyl carbonate), PG681 (Triptolide 14-(R)-α-methyl-tert-butoxycarbonylmethyl carbonate), PG682 (Triptolide 14-dimethylaminoethyl carbonate), PG682 PTSA (Triptolide 14-dimethylaminoethyl carbonate, p-toluenesulfonate salt), PG687 (Triptolide 14-hydroxycarbonylmethyl carbonate), PG687 Na (Triptolide 14-hydroxycarbonylmethyl carbonate, sodium salt), PG687 tris (Triptolide 14 hydroxycarbonylmethyl carbonate, tris (hydroxymethyl)aminomethane salt), PG688 (Triptolide 14-dimethylaminoethyl carbamate), and PG695 (Triptolide 14-tert-butyl carbonate).

* * * * *